(12) United States Patent
Lindsey et al.

(10) Patent No.: US 8,212,023 B2
(45) Date of Patent: Jul. 3, 2012

(54) METHODS AND INTERMEDIATES FOR THE SYNTHESIS OF PORPHYRINS

(75) Inventors: Jonathan S. Lindsey, Raleigh, NC (US); Masahiko Taniguchi, Raleigh, NC (US); Dazhong Fan, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 13/014,914

(22) Filed: Jan. 27, 2011

(65) Prior Publication Data
US 2011/0144325 A1    Jun. 16, 2011

Related U.S. Application Data

(62) Division of application No. 12/361,715, filed on Jan. 29, 2009, now Pat. No. 7,951,939, which is a division of application No. 11/192,934, filed on Jul. 29, 2005, now Pat. No. 7,501,508.

(51) Int. Cl.
*C07D 487/22* (2006.01)
*C07B 47/00* (2006.01)

(52) U.S. Cl. ........................................................ 540/145

(58) Field of Classification Search .................. 540/145; 514/185, 410; 424/9.61
See application file for complete search history.

(56) References Cited

U.S. PATENT DOCUMENTS

| | | | |
|---|---|---|---|
| 5,760,217 A | 6/1998 | Wijesekera et al. |
| 6,603,070 B2 | 8/2003 | Lindsey et al. |
| 2004/0023941 A1 | 2/2004 | Crapo et al. |
| 2004/0259810 A1 | 12/2004 | Grierson et al. |
| 2005/0096465 A1 | 5/2005 | Lindsey et al. |

OTHER PUBLICATIONS

Clarke et al. "Selective Synthesis of Asymmetrically Substituted 5,15-Diphenylporphyrins" *Tetrahedron Letters* 39:7167-7168 (1998).
Elgie et al. "Application of combinatorial techniques in the synthesis of unsymmetrically substituted 5,15-diphenylporphyrins" *Tetrahedron Letters* 41:2753-2757 (2000).
Hombrecher et al. "Synthese von 5,15-diarylsubstituiertern Porphyrinen über Aminomethylierung von Bis(4-ethyl-3-methyl-2-pyrryl)phenylmethanen" *Liebigs Ann. Chem.* 219-227 (1991).
International Search Report and Written Opinion for PCT/US06/25164; date of mailing Feb. 20, 2007.
Love et al. "The syntheses and structures of Group 1 expanded dipyrrolides: the formation of a 12-rung amidolithium circular ladder" *Chem. Commun.* 1682-1683 (2003).
Reid et al. "Double-stranded, [4+4] helicates of Fe(II) and Mn(II) supported by an extended dipyrrolide ligand" *Dalton Trans.* 4387-4388 (2003).
Schell et al. "Synthesis and Investigation of Glycosylated Mono- and Diarylporphyrins for Photodynamic Therapy" *Bioorganic & Medicinal Chemistry* 7:1857-1865 (1999).
Sutton et al. "Functionalized diphenylchlorins and bacteriochlorins: their synthesis and bioconjugation for targeted photodynamic therapy and tumour cell imaging" *Journal of Porphyrins and Phthalocyanines* 4:655-658 (2000).
Sutton et al. "Porphyrin, Chlorin, and Bacteriochlorin Isothiocyanates: Useful Reagents for the Synthesis of Photoactive Bioconjugates" *Bioconjugate Chem.* 13:249-263 (2002).

*Primary Examiner* — Paul V. Ward
(74) *Attorney, Agent, or Firm* — Myers Bigel Sibley & Sajovec, P.A.

(57) ABSTRACT

A method of making a porphyrin is carried out by: (a) condensing (i) a 1,9-bis(N,N-)dialkylaminomethyl)dipyrromethane of Formula II:

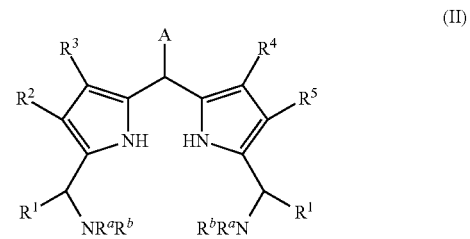

with (ii) a dipyrromethane to produce a reaction product; then (b) oxidizing the reaction product; and then (c) optionally demetallating said reaction product to produce the porphyrin. The reaction is particularly useful for making substituted porphyrins with a wide range of substituents at the A and/or B (the 5 and/or 15) positions.

6 Claims, 1 Drawing Sheet

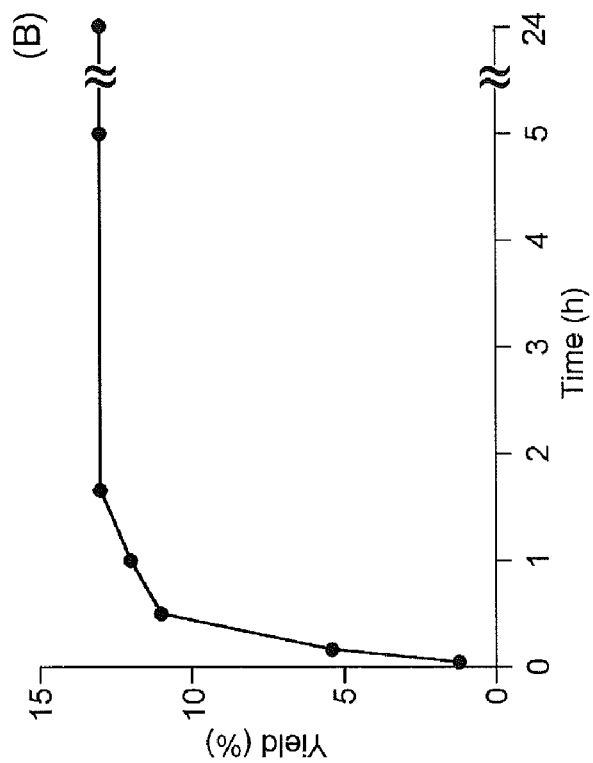
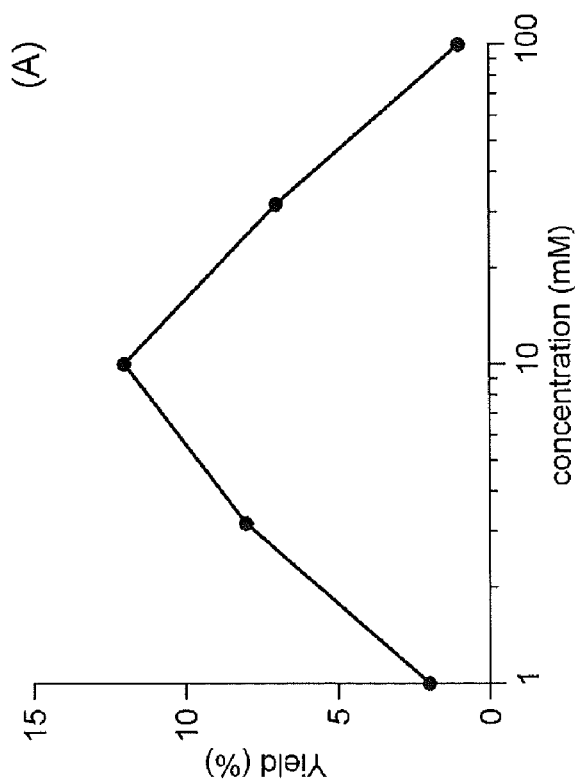

METHODS AND INTERMEDIATES FOR THE SYNTHESIS OF PORPHYRINS

RELATED APPLICATIONS

This application claims priority to and is a divisional of U.S. patent application Ser. No. 12/361,715, filed Jan. 29, 2009, now U.S. Pat. No. 7,951,939, which is a divisional of U.S. patent application Ser. No. 11/192,934, filed Jul. 29, 2005, now U.S. Pat. No. 7,501,508, the disclosure of each of which is incorporated by reference herein in its entirety.

This application is also related to Jonathan S. Lindsey, Masahiko Taniguchi, Arumugham Balakumar, and Dazhong Fan, U.S. patent application Ser. No. 12/494,711, filed Jun. 30, 2009, and published as US 2009/0270638, which is a divisional of U.S. patent application Ser. No. 11/193,562, Methods and Intermediates for the Synthesis of Porphyrins, filed Jul. 29, 2005, now U.S. Pat. No. 7,582,751, the disclosure of each of which is incorporated by reference herein in its entirety.

GOVERNMENT FUNDING

This invention was made with US Government support under Grant Number GM36238 from the National Institutes of Health. The Government has certain rights to this invention.

FIELD OF THE INVENTION

The present invention concerns methods for making porphyrins, including but not limited to trans-A,B-porphyrins, with 1,9-bis(N,N-dialkylaminomethyl) dipyrromethane intermediates.

BACKGROUND OF THE INVENTION

Porphyrins bearing only one or two substituents present a compact architecture suitable for a wide variety of applications or further synthetic elaboration. For substituents at the meso-positions, the methodology established for preparing porphyrins bearing four distinct meso-substituents would appear applicable. The route to such ABCD-porphyrins entails condensation of a dipyrromethane+dipyrromethane-1,9-dicarbinol, where the four substituents are introduced via the meso-positions of both dipyrromethane species and the carbinol units at the 1- and 9-positions.[1] The corresponding synthesis of A-porphyrins, trans-AB-porphyrins, (and also trans-$A_2$-porphyrins)[2] would employ meso-substituted dipyrromethanes with no substituents at the carbinol sites. To our surprise, condensations with dipyrromethanes bearing primary carbinol groups proceeded poorly, giving a mixture of porphyrins and overall low yields.[3] No better alternatives (other than statistical condensations) to A-porphyrins or trans-AB-porphyrins have been developed. This limitation prompted us to investigate C1 synthons having greater reactivity than primary carbinol groups for the rational synthesis of porphyrins bearing one or two meso-substituents.

A wide variety of C1 synthons have been employed in porphyrin chemistry, either as functional groups (aldehyde,[4] hydroxymethyl[3]) attached to a pyrrolic species or as added reagents (formic acid,[5] trimethyl orthoformate,[5,6] formaldehyde,[7] and imines[8]). A key consideration in the use of dipyrromethanes is the possibility of acidolysis followed by undesired recombination of dipyrromethane-derived fragments, affording undesired porphyrin species (i.e., scrambling). The possibility of scrambling constrains the nature of the reactive groups employed as C1 synthons (e.g., aldehyde or hydroxymethyl) and reaction conditions that can be employed.

The aminomethyl group is an attractive candidate for the C1 synthon leading to porphyrinic macrocycles because of ease of introduction, the possibility that reaction can be carried out without added acid catalysts, and biomimetic analogy. Indeed, an aminomethylpyrrole (porphobilinogen, A)[9] is the biosynthetic precursor of all naturally occurring porphyrinic macrocycles (Chart 1). Aminomethylpyrroles have been prepared by the condensation of pyrrole derivatives with aldehydes and amines.[10] The advent of N,N-dimethylmethyleneammonium iodide (Eschenmoser's reagent),[11] designed for reactions with corrins, also facilitated the synthesis of aminomethylpyrrolic compounds. To construct porphyrinic macrocycles from aminomethylpyrroles, three different approaches have been investigated: (1) self-condensation of an aminomethylpyrrole (e.g., B or C),[12] (2) condensation of a bis(aminomethyl)pyrrole (e.g., D or E) with a pyrrole derivative,[12-14] and (3) 3+1 condensation of a bis(aminomethyl) pyrrole D with a tripyrrane.[14,15] These approaches are attractive in their simplicity but have the potential limitation of forming a mixture of porphyrin regioisomers depending on the β-substitution pattern of the pyrrolic substrates.

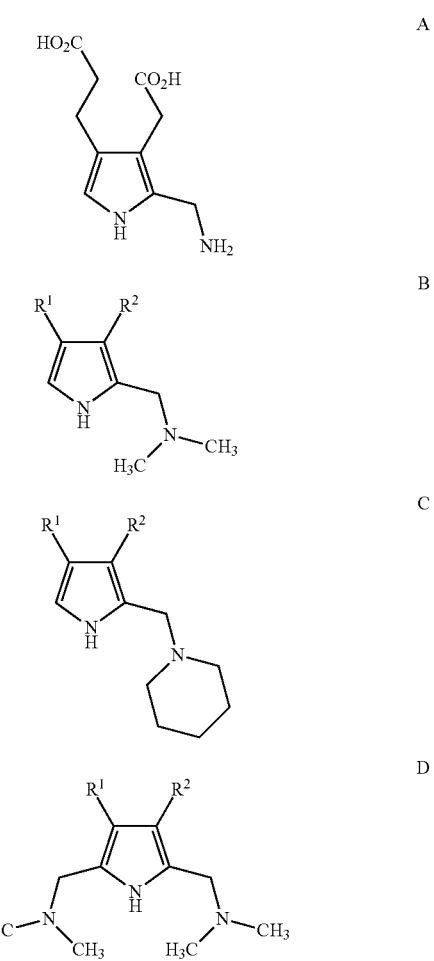

Chart 1

-continued

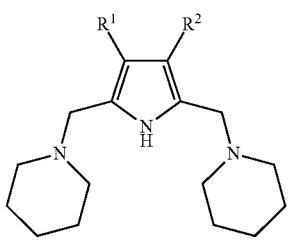

R¹, R² = H, CH₃, C₂H₅, C₆H₅, etc.

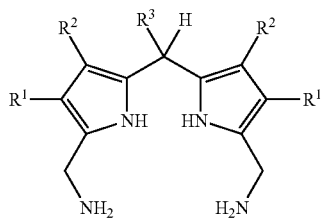

R¹ = H, Ph
R², R³ = CH₃, C₂H₅

Although aminomethyl-dipyrromethanes can be attractive precursors for porphyrinic macrocycles, aminomethyl-dipyrromethane derivatives (F) have been mainly used for the synthesis of expanded porphyrins, such as porphocyanine.[16] To our knowledge, the only previous example of aminomethyl-dipyrromethane derivatives in porphyrin chemistry is Hombrecher's synthesis of meso-substituted etioporphyrins:[17] treatment of a dipyrromethane with a Mannich reagent ($CH_2=NEt_2Cl$) gave the 1,9-bis(N,N-diethylaminomethyl) dipyrromethane (not isolated), which upon condensation with a dipyrromethane in situ afforded a mixture including a trans-AB-porphyrin, A-porphyrins, and etioporphyrin (Scheme 1).

Scheme 1

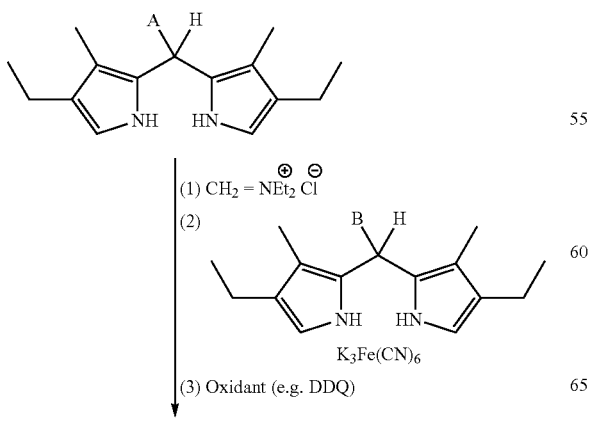

-continued

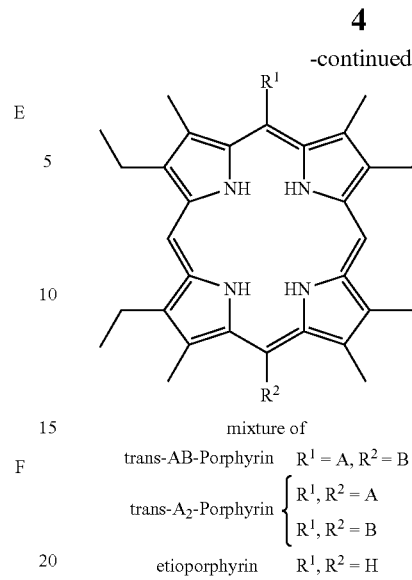

mixture of
trans-AB-Porphyrin  R¹ = A, R² = B
trans-A₂-Porphyrin { R¹, R² = A
                    { R¹, R² = B
etioporphyrin       R¹, R² = H

SUMMARY OF THE INVENTION

A first aspect of the invention is a method of making a porphyrin of Formula I:

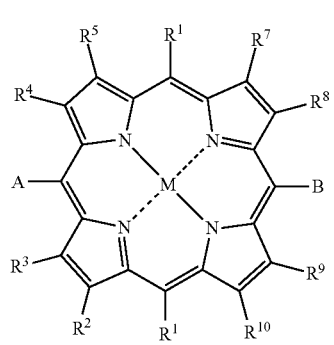

(I)

wherein:

A and B are each independently H or any suitable organic substituent;

R¹ is selected from the group consisting of H, alkyl and aryl;

R², R³, R⁴, R⁵, R⁷, R⁸, and R¹⁰ are each independently selected from the group consisting of H, halo, loweralkoxy, and loweralkylthio; and M is a metal or a pair of hydrogen atoms. The method comprises:

(a) condensing: (i) a 1,9-bis(N,N-dialkylaminomethyl) dipyrromethane of Formula II:

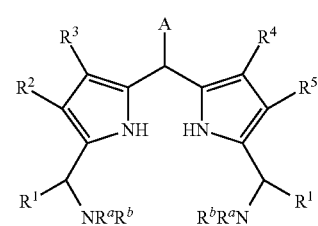

(II)

wherein $R^a$ and $R^b$ are each independently selected loweralkyl, and A, $R^1$, $R^2$, $R^3$, $R^4$, and $R^5$ are as given above, with
(ii) a dipyrromethane of Formula III:

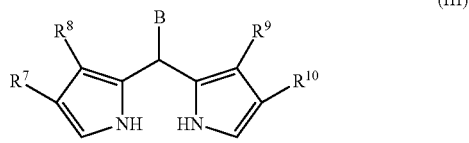

(III)

wherein B, $R^7$, $R^8$, $R^9$ and $R^{10}$ are as given above; in an alcohol solvent containing a metal salt to produce a reaction product; then (b) oxidizing said reaction product with an oxidizing agent and then (c) optionally demetallating said reaction product to produce the porphyrin of Formula I.

A second aspect of the invention is a compound of Formula II:

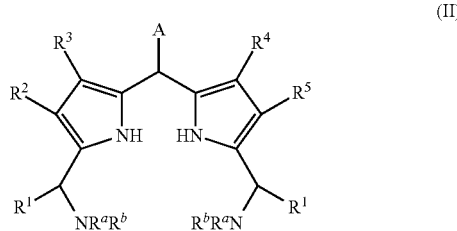

(II)

wherein:
$R^a$ and $R^b$ are each independently loweralkyl; and
A, $R^1$, $R^2$, $R^3$, $R^4$, and $R^5$ are as described above.

The foregoing and other objects and aspects of the invention are explained in greater detail in the drawings herein and the specification set forth below.

BRIEF DESCRIPTION OF THE DRAWINGS

FIG. 1. (A) Effect of concentration of dipyrromethane species in porphyrin formation (3a+1b). Reaction conditions were as follows: [Zn(OAc)$_2$ (10 equiv) in EtOH at reflux in air for 5 h, data points are 1, 3.16, 10, 31.6, 100, and 316 mM], then treated with ¾ equiv of DDQ per pyrrole unit. The yields of porphyrin were determined using absorption spectroscopy by removing small aliquots from the reaction mixture. (B) The yield of porphyrin as a function of time upon reaction of bis(N,N-dimethylaminomethyl)dipyrromethane 3a+dipyrromethane 1b with Zn(OAc)$_2$ under reflux in EtOH (the concentration of each reactant is 10 mM) exposed to air.

The present invention is explained in greater detail in the specification set forth below.

DETAILED DESCRIPTION OF THE PREFERRED EMBODIMENTS

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Hydroxyl" as used herein refers to an —OH group.

"Nitro" as used herein refers to an —NO$_2$ group.

"Alkyl" as used herein alone or as part of another group, refers to a straight or branched chain hydrocarbon containing from 1 to 10, 20, 40 or 50 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl —S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1 or 2.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. "Aryl" includes aromatic heterocyclic groups or heterocyclo groups as discussed below. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl; cycloalkylalkyl, aryl, arylalkyl, heterocyclo, heterocycloalkyl.

"Monosubstituted-amino" as used herein alone or as part of another group means the radical —NHR, where R is selected from the groups alkyl, haloalkyl, alkenyl, alkynyl, cycloalkyl, cycloalkylalkyl, aryl, arylalkyl, heterocyclo, heterocyclo alkyl.

"Amine" as used herein refers to amino, monosubstituted-amino, disubstituted-amino.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —$C(O)NR_aR_b$ radical, where $R_a$ and $R_b$ are any suitable substituent such as alkyl, cycloalkyl, alkenyl, alkynyl or aryl.

"Sulfonamide" as used herein alone or as part of another group refers to a —$S(O)_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —$N(R_c)C(O)NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —$N(R_a)C(O)OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —$OC(O)NR_aR_b$ radical, where $R_a$ and $R_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aromatic and nonaromatic (e.g., saturated or partially unsaturated aliphatic) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-$S(O)_m$, haloalkyl-$S(O)_m$, alkenyl-$S(O)_m$, alkynyl-$S(O)_m$, cycloalkyl-$S(O)_m$, aryl-$S(O)_m$, arylalkyl-$S(O)_m$, heterocyclo-$S(O)_m$, heterocycloalkyl-$S(O)_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Dipyrromethane" as used herein includes both unsubstituted and substituted dipyrromethanes, which may be unsubstituted or substituted one or more times at the 1, 2, 3, 5, 7, 8 or 9 positions with any suitable substituent such as halo, carbonyl, alkyl, fluoroalkyl including perfluoroalkyl, aryl (e.g., A or B at the 5 position; dialkylaminomethyl alkyl at the 1 and 9 positions), Dipyrromethanes may be coupled to porphyrinic macrocycles at any suitable position on the dipyrromethanes, including the 1, 2, 3, 5, 7, 8, or 9 position, and particularly the 5 position.

"Metal" as used herein is any suitable metal, including but not limited to Cu, Zn, Mg, Pt, Pd, Sn, Ni, and Al.

"Metal salt" as used herein includes but is not limited to zinc, palladium, copper, nickel, or cobalt salts. Zinc salts are currently preferred. The salts may be formed with any suitable counterion(s), including but not limited to acetate, chloride, acac (acetylacetate), etc.

"Surface attachment group" may be any reactive substituent useful for attaching a compound to a substrate such as a metal, insulator, semiconductor substrate or polymer, which reactive substituent may be coupled directly to the parent molecule or coupled to the parent molecule by a linker included as a portion of the surface attachment group. When the linker is aromatic the surface attachment group is said to be aromatic.

"Cross-coupling group" may be any reactive substituent useful for coupling a compound to another compound such as another porphyrin, as a semiconductor substrate or polymer, which reactive substituent may be coupled directly to the parent molecule or coupled to the parent molecule by a linker included as a portion of the cross-coupling group. When the linker is aromatic the cross-coupling group is said to be aromatic.

"Bioconjugatable group" may be any reactive substituent or member of a specific binding pair useful for attaching a compound to another organic compound such as a protein, peptide, nucleic acid (e.g., DNA, RNA), which reactive substituent or member of a specific binding pair may be coupled directly to the parent molecule or coupled to the parent molecule by an linker included as a portion of the bioconjugatable group. When the linker is aromatic the bioconjugatable group is said to be aromatic.

"Hydrophilic group" refers to any aromatic or aliphatic group that is water soluble or enhances the water solubility of the corresponding compound to which it is coupled. Hydrophilic groups may be coupled directly to the parent molecule or coupled to the parent molecule by a linker included as a portion of the hydrophilic group. When the linker is aromatic the bioconjugatable group is said to be aromatic.

"Linkers" are aromatic or aliphatic groups (which may be substituted or unsubstitued and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

The disclosures of all United States Patent references cited herein are to be incorporated by reference herein as if fully set forth.

A. Surface Attachment Groups.

As noted above, compounds of the invention can be substituted with a surface attachment group, which may be in protected or unprotected form. A surface attachment group may be a reactive group coupled directly to the azolo group, or coupled to the azolo group by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to:
4-carboxyphenyl,
carboxymethyl,
2-carboxyethyl,
3-carboxypropyl,
2-(4-carboxyphenyl)ethynyl,
4-(2-(4-carboxyphenyl)ethynyl)phenyl,
4-carboxymethylphenyl,
4-(3-carboxypropyl)phenyl,
4-(2-(4-carboxymethylphenyl)ethynyl)phenyl;
4-hydroxyphenyl,
hydroxymethyl,
2-hydroxyethyl,
3-hydroxypropyl,
2-(4-hydroxyphenyl)ethynyl,
4-(2-(4-hydroxyphenyl)ethynyl)phenyl,
4-hydroxymethylphenyl,
4-(2-hydroxyethyl)phenyl,
4-(3-hydroxypropyl)phenyl,
4-(2-(4-hydroxymethylphenyl)ethynyl)phenyl;
4-mercaptophenyl,
mercaptomethyl,
2-mercaptoethyl,
3-mercaptopropyl,
2-(4-mercaptophenyl)ethynyl,
4-(2-(4-mercaptophenyl)ethynyl)phenyl,
4-mercaptomethylphenyl,
4-(2-mercaptoethyl)phenyl,
4-(3-mercaptopropyl)phenyl,
4-(2-(4-mercaptomethylphenyl)ethynyl)phenyl;
4-selenylphenyl,
selenylmethyl,
2-selenylethyl,
3-selenylpropyl,
2-(4-selenylphenyl)ethynyl,
4-selenylmethylphenyl,
4-(2-selenylethyl)phenyl,
4-(3-selenylpropyl)phenyl,
4-selenylmethylphenyl,
4-(2-(4-selenylphenyl)ethynyl)phenyl;
4-tellurylphenyl,
tellurylmethyl,
2-tellurylethyl,
3-tellurylpropyl,
2-(4-tellurylphenyl)ethynyl,
4-(2-(4-tellurylphenyl)ethynyl)phenyl,
4-tellurylmethylphenyl,
4-(2-tellurylethyl)phenyl,
4-(3-tellurylpropyl)phenyl,
4-(2-(4-tellurylmethylphenyl)ethynyl)phenyl;
4-(dihydroxyphosphoryl)phenyl,
(dihydroxyphosphoryl)methyl,
2-(dihydroxyphosphoryl)ethyl,
3-(dihydroxyphosphoryl)propyl,
2-[4-(dihydroxyphosphoryl)phenyl]ethynyl,
4-[2-[4-(dihydroxyphosphoryl)phenyl]ethynyl]phenyl,
4-[(dihydroxyphosphoryl)methyl]phenyl,
4-[2-(dihydroxyphosphoryl)ethyl]phenyl, 4-[2-[4-(dihydroxyphosphoryl)methylphenyl]ethynyl]phenyl;
4-(hydroxy(mercapto)phosphoryl)phenyl,
(hydroxy(mercapto)phosphoryl)methyl,
2-(hydroxy(mercapto)phosphoryl)ethyl,
3-(hydroxy(mercapto)phosphoryl)propyl,
2-[4-(hydroxy(mercapto)phosphoryl)phenyl]ethynyl,
4-[2-[4-(hydroxy(mercapto)phosphoryl)phenyl]ethynyl]phenyl,
4-[(hydroxy(mercapto)phosphoryl)methyl]phenyl,
4-[2-(hydroxy(mercapto)phosphoryl)ethyl]phenyl,
4-[2-[4-(hydroxy(mercapto)phosphoryl)methylphenyl]ethynyl]phenyl;
4-cyanophenyl,
cyanomethyl,
2-cyanoethyl,
3-cyanopropyl,
2-(4-cyanophenyl)ethynyl,
4-[2-(4-cyanophenyl)ethynyl]phenyl,
4-(cyanomethyl)phenyl,
4-(2-cyanoethyl)phenyl,
4-[2-[4-(cyanomethyl)phenyl]ethynyl]phenyl;
4-cyanobiphenyl;
4-aminophenyl,
aminomethyl,
2-aminoethyl,
3-aminopropyl,
2-(4-aminophenyl)ethynyl,
4-[2-(4-aminophenyl)ethynyl]phenyl,
4-aminobiphenyl;
4-formylphenyl,
4-bromophenyl,
4-iodophenyl,
4-vinylphenyl,
4-ethynylphenyl,
4-allylphenyl,
4-[2-(trimethylsilyl)ethynyl]phenyl,
4-[2-(triisopropylsilyl)ethynyl]phenyl,
4-(4,4,5,5-tetramethyl-1,3,2-dioxaborolan-2-yl)phenyl;
formyl,
bromo,
iodo,
bromomethyl,
chloromethyl,
ethynyl,
vinyl,
allyl;
4-(ethynyl)biphen-4'-yl,
4-[2-(triisopropylsilyl)ethynyl]biphen-4'-yl,
3,5-diethynyiphenyl;
4-(bromomethyl)phenyl, and
2-bromoethyl.

In addition to the monodentate linker-surface attachment groups described above, multidentate linkers can be employed [Nikitin, K. *Chem. Commun.* 2003, 282-283; Hu, J.; Mattern, D. L. *J. Org. Chem.* 2000, 65, 2277-2281; Yao, Y.; Tour, J. M. *J. Org. Chem.* 1999, 64, 1968-1971; Fox, M. A. et al. *Langmuir*, 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science,* 2001, 494, 1-20; Whitesell, J. K.; Chang, H. K. *Science,* 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:
1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl]methyl}phenyl,
1,1,1-tris[4-dihydroxyphosphorylmethyl)phenyl]methyl, and
4-{1,1,1-tris[4-(dihydroxyphosphorylmethyl)phenyl]methyl}phenyl;
All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to:
Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.
Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4'-yl,
Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc.,
Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc.,
Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl, 4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.

Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

B. Cross-Coupling Groups.

Compounds produced of the present invention, as individual ring systems or as constituents of sandwich coordination compounds, can be coupled together as linear polymers in like manner as described in U.S. Pat. No. 6,777,516 to Li, Gryko and Lindsey. Examples of suitable linking or cross-coupling groups include but are not limited to groups $J^2$ and $J^3$ below, which may be linked directly to the compound of the invention or by an intervening linker L. Linkers L can be aryl, alkyl, heteroaryl, heteroalkyl (e.g., oligoethylene glycol), peptide, polysaccharide, etc. The cross-coupling group may be simply a reactive attachment group or moiety (e.g., —R' where R' is a reactive group such as bromo), or may comprise a combination of an intervening linker group coupled to a reactive group (e.g., —R"R', where R' is a reactive group and R" is an intervening group such as a hydrophilic group).

Particular examples of linkers include, but are not limited to, 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, and 4,4"-terphenyl.

Dyads. The synthesis of dyads of compounds of the invention can proceed via several different types of reactions. The reactions of interest include Glaser (or Eglinton) coupling of two identical porphyrins (generating a butadiyne linker), Cadiot-Chodkiewicz coupling of two porphyrins (generating a butadiyne linker), Sonogashira coupling of two different porphyrins (generating an ethyne linker), Heck or Wittig reactions of two different porphyrins (generating an alkene linker), Suzuki coupling of two different porphyrins (generating a phenylene or biphenyl linker), etc. Other reactions can also be employed.

| $J^1$—L—TD—L—$J^2$ + $J^3$—L—TD—L—$J^4$ | | |
|---|---|---|
| $J^2$ | $J^3$ | Reaction Type |
| —B(OH)$_2$ | —Cl, —Br, —I | Suzuki |
| —≡—H | —Cl, —Br, —I | Sonogashira |
| —≡—H | —≡—H | Glaser |
| —≡—H | —≡—X | Cadiot-Chodkiewicz |
| —CHO | —Br, —I | Wittig |
| —HC=CH$_2$ | —Br, —I | Heck |

Polymers. The methods for synthesis of polymeric arrays of compounds include but are not restricted to use of the following types of reactions:

Glaser (or Eglinton) coupling of a monomeric porphyrins (generating a butadiyne linker)
Cadiot-Chodkiewicz coupling of two different compounds (generating a butadiyne linker joining a block copolymer)
Sonogashira coupling of two different compounds (generating an ethyne linker joining a block copolymer)
Heck or Witting reactions of two different compounds (generating an alkene linker joining a block copolymer)
Suzuki coupling of two different compounds (generating a phenylene or biphenyl linker joining a block copolymer)
We also can polymerize compounds bearing substituents such as two or more thiophene groups (generating an oligothiophene linker) or two or more pyrrole groups (generating a polypyrrole linker).

The synthesis of the polymers can be performed using stepwise methods or using polymerization methods. Both methods generally require two reactive groups attached to the porphyrin in order to prepare a polymer where the porphyrins are integral components of the polymer backbone. (An alternative design yields pendant polymers where the porphyrins are attached via one linkage to the polymer backbone.) The stepwise synthetic method generally requires the use of protecting groups to mask one reactive site, and one cycle of reactions then involves coupling followed by deprotection. In the polymerization method no protecting groups are employed and the polymer is prepared in a one-flask process.

The polymerizations can take place in solution or can be performed with the polymer growing from a surface. The polymerization can be performed beginning with a solid support as in solid-phase peptide or DNA synthesis, then removed, purified, and elaborated further for specific applications. The polymerization can also be performed with the nascent polymer attached to an electroactive surface, generating the desired electronic material in situ.

C. Bioconjugatable Groups.

Biconjugatable groups may be included in compounds of the invention to provide a reactive site for conjugation so that the compounds may be coupled to or conjugated to other groups, such as proteins, peptides, targeting agents such as antibodies, polymers, particles such as nanoparticles, organic, polymeric or inorganic beads, other solid support surfaces, etc, to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R' is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidium, pyridinium). Bioconjugatable groups include amines (including amine derivatives) such as isocyanates, isothiocyanates, iodoacetamides, azides, diazonium salts, etc. acids or Acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Linking groups such as the foregoing are known and described in U.S. Pat. Nos. 6,728,129; 6,657,884; 6,212, 093; and 6,208,553.

Conjugates. Other groups can be attached to the compounds of the invention to form a conjugate by means of a cross-coupling group or bioconjugatable group to tune or adjust the solubility properties of the compound, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acid may be attached by means of the linking group. Particles such as nanoparticles, glass beads, etc. may be attached by means of the linking group. Where such additional compounds are attached to form a conjugate thay may be attached directly to the compound or attached by means of an intervening group such as a hydrophilic group, depending upon the particular linking group employed (as noted above).

Hydrophilic groups. Compounds of the present invention may include hydrophilic groups coupled thereto as groups A and/or B, e.g., covalently coupled thereto directly or by an intervening linker, to facilitate delivery thereof, or improve stability, in accordance with known techniques. Suitable hydrophilic groups are typically polyols or polyalkylene oxide groups, including straight and branched-chain polyols, with particular examples including but not limited to poly (propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716, 811; and 6,720,306. For example, compounds can be pegylated using a single 40,000 molecular weight polyethylene glycol moiety that is attached to the compound by means of a linking group.

D. Reactions.

As noted above, the present invention provides a method of making a porphyrin of Formula I:

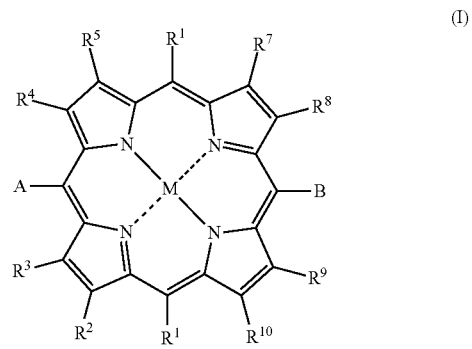

wherein:

A and B are each independently H or a suitable organic substituent (e.g., alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, mercapto, azido, cyano, hydroxyl, nitro, acyl, alkoxy, alkylthio, amino, alkylamino, arylalkylamino, disubstituted amino, acylamino, acyloxy, amide, sulfonamide, urea, alkoxyacylamino, aminoacyloxy, hydrophilic groups, surface attachment groups, cross-coupling groups or bioconjugatable groups);

$R^1$ is selected from the group consisting of H, alkyl and aryl;

$R^2$, $R^3$, $R^4$, $R^5$, $R^7$, $R^8$, $R^9$, and $R^1$ are each independently selected from the group consisting of H, halo, loweralkoxy, and loweralkylthio, are more preferably H or halo, and are most preferably H; and M is a metal or a pair of hydrogen atoms.

The method comprises: (a) condensing (i) a 1,9-bis(N,N-)dialkylaminomethyl) dipyrromethane of Formula II:

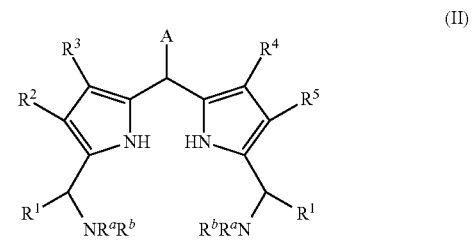

wherein $R^a$ and $R^b$ are each independently selected loweralkyl, and A, $R^1$, $R^2$, $R^3$, $R^4$, and $R^5$ are as given above, with (ii) a dipyrromethane of Formula III:

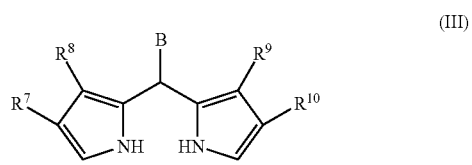

wherein B, $R^7$, $R^8$, $R^9$ and $R^{10}$ are as given above; in an alcohol solvent containing a metal salt to produce a reaction product; and then (b) oxidizing the reaction product with an oxidizing agent and then (c) optionally demetallating the reaction product to produce the porphyrin of Formula I. The reaction conditions are not critical. Any suitable alcohol can be used as the solvent, including methanol, ethanol, propanol, isopropanol, and mixtures thereof. Examples of suitable metal salts include but are not limited to zinc, palladium, copper, nickel and cobalt salts. Suitable oxidizing agents include quinone oxidizing agents such as dichlorodicyanobenzoquinone (DDQ), p-chloranil, and o-chloranil. The demetallating step can be carried out in accordance with known techniques by treating or mixing the metallated compound with any suitable acid (e.g., acetic acid, trifluoroacetic acid, hydrochloric acid, sulfuric acid, etc.).

In some embodiments suitable groups "A" and "B" include but are not limited to alkene, alkyne, alcohol, thiol, selenyl, phosphono, carboxylic acid, formyl, halo or amine group, which may be linked directly to the parent molecule or indirectly by means of an intervening linker group as noted above.

In some embodiments A is a bioconjugatable group and B is a hydrophilic group, or A is a hydrophilic group and B is a biconjugatable group. In such embodiments either, or both, of A and B are aliphatic (including any linker that is incorporated into the hydrophilic group or bioconjugatable group to couple it to the core molecule, and hence excluding aromatic linkers).

A compound of Formula II as given above can be made by reacting a dipyrromethane of Formula IV:

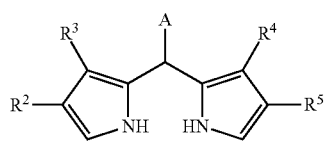

(wherein A, $R^2$, $R^3$, $R^4$ and $R^5$ are as given above) with an N,N-dialkylmethylammonium halide of Formula V:

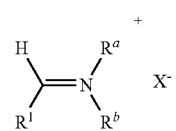

wherein $R^a$, $R^b$ and $R^1$ are as given above, and X is halo, in a suitable solvent to produce said compound of Formula II. The reaction conditions are not critical. Temperatures can be, for example, room temperature to 100° C. Suitable solvents are, in general, polar or nonpolar aprotic solvents such as methylene chloride, chloroform, tetrahydrofuran, nitromethane, toluene, acetonitrile, or mixtures thereof.

Compounds of Formulas III and IV can be made in accordance with known techniques for the synthesis of dipyrromethanes, or variations thereof that will be apparent to persons skilled in the art. Compounds of Formula V can be made in accordance with known techniques for the production of Eschenmoser's reagent, or variations thereof that will be apparent to persons skilled in the art.

E. Utility.

Porphyrins produced by the methods and intermediates described herein are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Compounds produced by the methods and intermediates of the invention are also useful immobilized to a substrate for making charge storage molecules and information storage devices containing the same. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The compounds can be coupled to substrates to form molecular batteries, molecular capacitors and electrochromic displays as described in U.S. Pat. No. 6,777,516 to Li et al. The porphyrin may comprise a member of a sandwich coordination compound in the information storage molecule, such as described in U.S. Pat. No. 6,212,093 to Li et al., U.S. Pat. No. 6,451,942 to Li et al., or U.S. Pat. No. 6,777,516 to Li et al.

Porphyrins produced by the methods of the invention are useful per se or in further modified form (e.g., as a salt, metalated compound, conjugate or prodrug) for diagnostic and therapeutic purposes in like manner as other compounds described for photodynamic therapy, such as described in US Patent Application Publication No. 2004/0044197 to Pandey et al.

The present invention is explained in greater detail in the following non-limiting Examples.

EXAMPLES

We here report the synthesis of trans-AB-, trans-$A_2$-, and A-porphyrins via a [2+2] condensation of a bis(aminomethyl)dipyrromethane+a dipyrromethane. The dipyrromethanes lack β-substituents. N,N-Dimethylaminomethylation of a dipyrromethane is achieved with Eschenmoser's reagent. The survey of the scope of reaction encompassed 14 dipyrromethanes and led to a survey of the synthesis of >40 zinc porphyrins.

Synthesis of aminomethyl derivatives of 5-phenyldipyrromethane. A series of aminomethyl derivatives of 5-phenyldipyrromethane was prepared as shown in Scheme 2. Treatment of 5-phenyldipyrromethane (1a)[18] with Eschenmoser's reagent[11] at room temperature smoothly gave the dipyrromethane-bis(ammonium iodide) 2a, which was easily isolated by precipitation upon addition of ethyl ether. Alternatively, treatment of the reaction mixture containing 2a with aqueous $NaHCO_3$ quantitatively gave the corresponding free amine, 1,9-bis(N,N-dimethylaminomethyl)dipyrromethane (3a). The reaction of 3a with methyl iodide gave the quaternized ammonium salt 4a.

Scheme 2

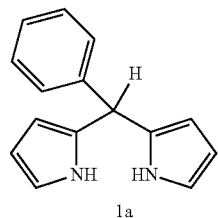

1a

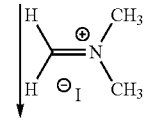

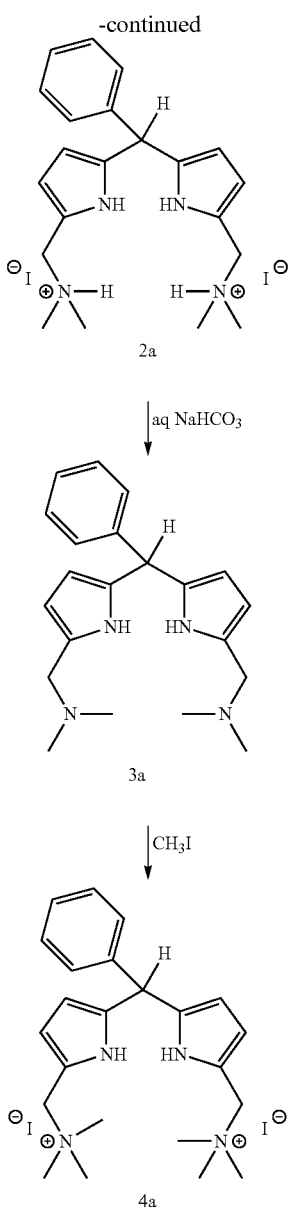

Optimization of the reaction conditions for porphyrin formation. Porphyrin formation via a [2+2] condensation was first examined by the reaction of free base bis(aminomethyl) dipyrromethane 3a+dipyrromethane 1b[19] under various conditions. In each case, the yield of porphyrin was determined by absorption spectroscopy and the occurrence of scrambling was assessed by laser-desorption mass spectrometry (LD-MS).[20, 21] Initially, several reagents (oxidant, acid, and metal template) were examined for the reaction in $CH_2Cl_2$/EtOH (3:1). The major findings are as follows:

(1) Oxidant: The condensation of 3a+1b in $CH_2Cl_2$/EtOH (3:1) under reflux for 16 h (without any oxidant other than air) gave no porphyrin (Table 1, Entry 1). However, further treatment of the reaction mixture with DDQ afforded free base porphyrin 5ab in 7% yield (Entry 2). Smith employed $K_3Fe(CN)_6$ as an oxidant for porphyrin formation from a bis(aminomethyl)pyrrole.[14] Inclusion of $K_3Fe(CN)_6$ in the condensation of 3a+1b afforded porphyrin 5ab in 5% yield (Entry 3). The yield increased to 7% upon further oxidation with DDQ (Entry 4). No added catalyst is required for formation of the putative porphyrinogen; however, oxidation cannot be achieved with air or $K_3Fe(CN)_6$ but requires use of DDQ.

(2) Acid: Trifluoroacetic acid, trichloroacetic acid, acetic acid, or propionic acid was examined as an acid catalyst (Entry 5). At room temperature, no porphyrin formation was observed.

(3) Metal template: The condensation of 3a+1b in the presence of $Zn(OAc)_2$ in $CH_2Cl_2$/EtOH (3:1) under reflux gave zinc porphyrin Zn5ab in 2% yield (Entry 6). Oxidation of the reaction mixture with DDQ afforded Zn5ab in up to 13% yield without scrambling (Entry 7). No free base porphyrin was detected. This method provides a simple procedure for the formation of a trans-AB-porphyrin.

The required reagents for the porphyrin-forming reaction from a bis(aminomethyl)dipyrromethane are $Zn(OAc)_2$ and DDQ. Further modification of the reaction conditions was investigated by changing the following factors:

(4) Solvent: EtOH gave the best result out of six solvents that were examined (THF, MeOH, toluene, $CH_2Cl_2$, $CHCl_3$, EtOH). In alcohol solvents, the reaction proceeded rapidly and was complete in 1 h. A longer reaction time was required with halogenated solvents.

(5) Amount of $Zn(OAc)_2$: The highest yield of porphyrin was obtained when 10 molar equivalents of $Zn(OAc)_2$ was used. The yield decreased to one third with a stoichiometric amount of $Zn(OAc)_2$.

(6) Concentration: The effects of reactant concentration were examined over the range from 1 mM to 316 mM. The highest yield (~12% spectroscopic yield) was obtained at 10 mM (FIG. 1A).

(7) Reaction time: The yield of porphyrin as a function of time upon condensation of 3a and 1b (to form porphyrin Zn5ab) is shown in FIG. 1B. The condensation was essentially complete within ~2 h.

From these studies, the best conditions for porphyrin formation are as follows: 3a (10 mM), 1b (10 mM), and $Zn(OAc)_2$ (10 equiv) in EtOH under reflux for ~2 h, followed by treatment with DDQ (¾ equiv per pyrrolic unit) at room temp for 15 min. Application of this method afforded trans-AB-porphyrin Zn5ab in 16% yield without detectable scrambling.

TABLE 1

Effect of reagents in porphyrin formation via 3a + 1b[a]

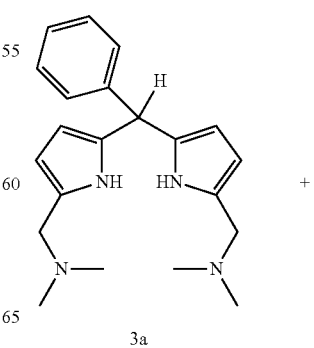

TABLE 1-continued

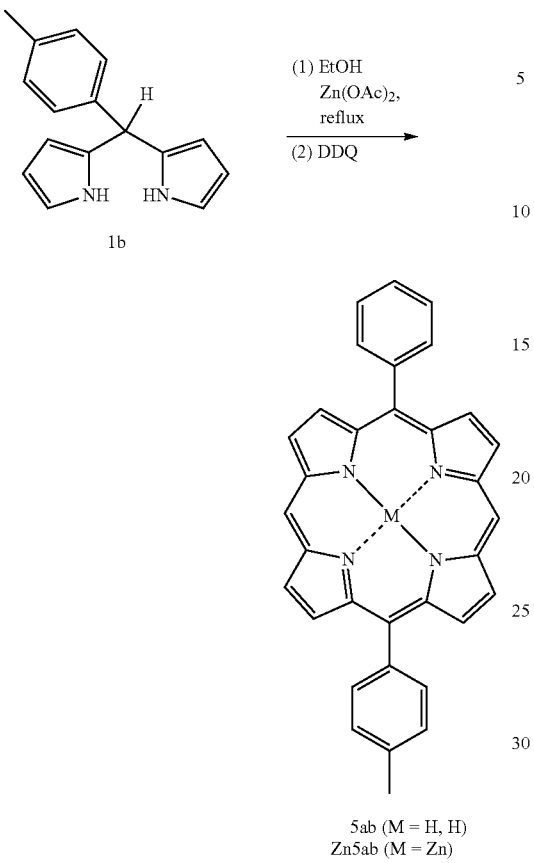

| Entry | Reagent 1 | Reagent 2 | Product | Yield (%)[b] |
|---|---|---|---|---|
| 1 | — | — | — | 0 |
| 2 | — | DDQ[c] | 5ab | 7 |
| 3 | K₃Fe(CN)₆ | — | 5ab | 5 |
| 4 | K₃Fe(CN)₆ | DDQ[c] | 5ab | 7 |
| 5 | acid[d] | DDC[c] | — | 0 |
| 6 | Zn(OAc)₂ | — | Zn5ab | 2 |
| 7 | Zn(OAc)₂ | DDQ[c] | Zn5ab | 13 |

[a]Reaction conditions: 10 mM reactants in CH₂Cl₂/EtOH (3:1) under reflux exposed to air for 18 h in the presence or absence of reagents [K₃Fe(CN)₆ (0.1, 1, or 10 equiv) or Zn(OAc)₂ (10 equiv)].
[b]The yields of porphyrin were calculated upon absorption spectroscopy of small aliquots from the reaction mixture
[c]Following the general reaction condition, the reaction mixture was treated with 3/4 equiv of DDQ per pyrrole unit (30 mM).
[d]Trifluoroacetic acid (TFA), trichloroacetic acid (TCA), acetic acid, or propionic acid.

Reactivity of free base amine (3a) versus ammonium salts (2a and 4a) of dipyrromethanes. The reactivity of free base amine (3a) versus amine salt (2a or 4a) was examined under the optimized conditions described above and also in the absence of Zn(OAc)₂ and/or DDQ (Table 2). The highest yields were obtained for all three substrates (2a, 3a, 4a) upon use of both Zn(OAc)₂ and DDQ. This result was somewhat surprising, because we anticipated that the quaternized ammonium salt might react in the absence of Zn(OAc)₂. With either Zn(OAc)₂ or DDQ present, the bis(ammonium) salts of the dipyrromethane (2a, 4a) exhibited reactivity comparable to each other and greater than that of the free base amine 3a. However, the highest yield overall was observed with the free base amine derivative 3a. All subsequent porphyrin-forming reactions were performed with free base 1,9-bis(N,N-dimethylaminomethyl)dipyrromethane analogues of 3a.

TABLE 2

Effect of reagents and amine [free amine (3a) versus amine salt (2a or 4a)] in porphyrin formation[a]

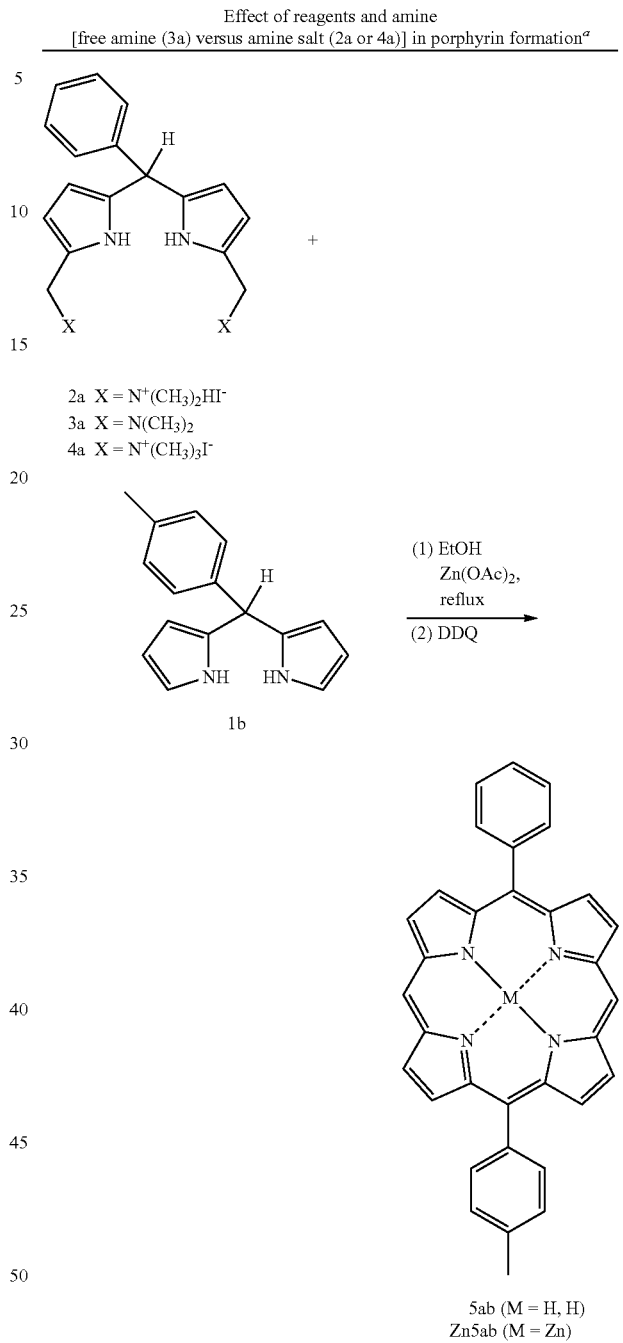

| Substrate | Step (1): Step (2): — — | — DDQ | Zn(OAc)₂ — | Zn(OAc)₂ DDQ |
|---|---|---|---|---|
| 2a | 1 (5ab) | 6 (5ab) | 4 Zn5ab[c] | 10 (Zn5ab) |
| 3a | 0 | 0 | 0 | 13 (Zn5ab) |
| 4a | <1 (5ab) | 6 (5ab) | 2 (Zn5ab) | 8 (Zn5ab) |

[a]Reaction conditions: 10 mM reactants and 10 equiv of Zn(OAc)₂ in EtOH under reflux exposed to air for 18 h, then treated with 3/4 equiv of DDQ per pyrrole unit (30 mM).
[b]The yields of porphyrin were calculated using absorption spectroscopy by removing small aliquots from the reaction mixture.
[c]LD-MS showed the presence of free base porphyrin 5ab.

Synthesis of trans-AB-, trans-A₂-, and A-porphyrins. Probing aryl/alkyl/H substituents. A series of known dipyrromethanes (1a-n)[1, 18, 19, 22-31] was prepared by application of a new solventless synthesis that entails treatment of an aldehyde dissolved in 100 equiv of pyrrole with a mild Lewis acid (InCl$_3$) at room temperature.[32] Each dipyrromethane (1a-n) was reacted with Eschenmoser's reagent at room temperature followed by workup with aqueous NaHCO$_3$ (aqueous K$_2$CO$_3$ was used for the synthesis of 3i), affording the corresponding free base 1,9-bis(N,N-dimethylaminomethyl)-dipyrromethane (3a-n) in 43% to 91% yield (Table 3).

TABLE 3

Synthesis of 5-substituted-1,9-bis(N,N-dimethylaminomethyl) dipyrromethanes 3a-n[a]

| R | | Yield (%)[b] |
|---|---|---|
| a | phenyl | 68 |
| b | 4-methylphenyl | 91 |
| c | 2,4,6-trimethylphenyl | 64 |
| d | 4-methoxyphenyl | 85 |
| e | pentafluorophenyl | 87 |
| f | —CH$_3$ | 68 |
| g | n-butyl | 87 |
| h | n-pentyl | 83 |
| i | —H | 63 |
| j | 5,5-dimethyl-1,3-dioxan-2-yl | 75 |
| k | allyl | 43 |

TABLE 3-continued

Synthesis of 5-substituted-1,9-bis(N,N-dimethylaminomethyl) dipyrromethanes 3a-n[a]

| R | Yield (%)[b] |
|---|---|
| l (branched alkyl) | 81 |
| m (CH₂C(O)OEt group) | 66 |
| n (≡–TMS) | 86 |

[a]Reaction conditions: 100 mM dipyrromethane 1a-n and 2 equiv of Eschenmoser's reagent in $CH_2Cl_2$ at room temperature for 1 h, then washed with saturated aqueous $NaHCO_3$ ($K_2CO_3$ for 1i).
[b]Isolated yield.

The scope of porphyrin formation was examined using the 1,9-bis(N,N-dimethylaminomethyl)dipyrromethanes (Scheme 3, Table 4). Emphasis was placed on (1) variation of the substituents, (2) assessment of any scrambling processes, and (3) yields of porphyrin. Altogether, the preparation of 28 trans-AB-porphyrins was examined. The yields of porphyrin were determined spectroscopically and ranged from <1% to 19% depending on the substituents and combination of the dipyrromethane precursors. Note that a given porphyrin can be made in two ways by switching the combination of the 1,9-bis(N,N-dimethylaminomethyl)-dipyrromethane (3) and dipyrromethane (1). For example, 1e+3d afforded the zinc porphyrin Zn5de in <1% yield while 1d+3e gave Zn5de in 15% yield. In all cases where the better of the two possible combinations was employed, the yields ranged from 12% to 19%. In those cases where the porphyrin was isolated (Zn5ab and Zn5ac), the isolated yields compared well with the spectroscopic yield. Scrambling was observed only in the reaction of 5-(pentafluorophenyl)dipyrromethane (1e)+1,9-bis(N,N-dimethylaminomethyl)-5-pentyldipyrromethane (3g) (8% yield, level 2 scrambling). The scrambling problem could be overcome by reversal of the substituents; thus, reaction of 1g+3e afforded the same target porphyrin in 15% yield with no detectable scrambling.

In general, the reaction of 5-(pentafluorophenyl)dipyrromethane (1e) proceeded in low yield and/or scrambling whereas the same meso-substituent could be well accommodated upon use of 1,9-bis(N,N-dimethylaminomethyl)-5-(pentafluorophenyl)-dipyrromethane (3e). Taken together, the results upon condensation of a dipyrromethane 1,9-bis(N,N-dimethylaminomethyl)dipyrromethane are superior to those of the reaction of a 1,9-bis(hydroxymethyl)-5-substituted-dipyrromethane+a 5-substituted-dipyrromethane, which resulted in extensive scrambling.[3]

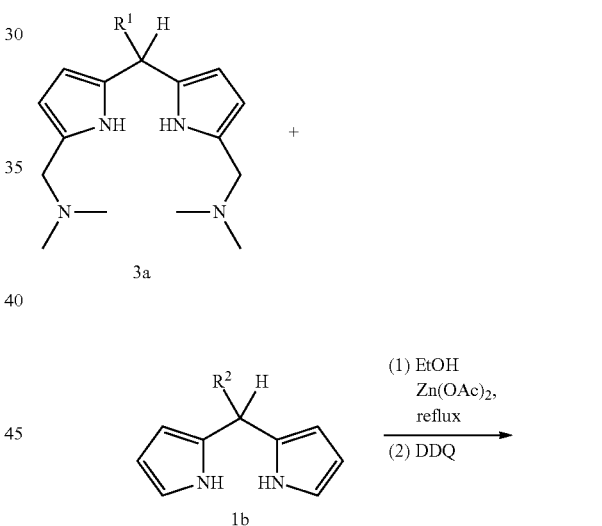

Scheme 3

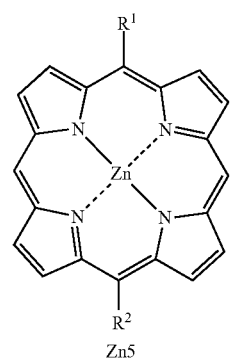

Zn5

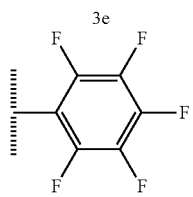
TABLE 4
Formation of trans-AB- and A-Porphyrins Zn5 via 3a-g,i + 1a-g,i[a]

TABLE 4-continued

Formation of trans-AB- and A-Porphyrins Zn5 via 3a-g,i + 1a-g,i[a]

| | | | | | |
|---|---|---|---|---|---|
| 1e | pentafluorophenyl | — | 4 | 8[c] | 2 |
| 1f | methyl | <u>12</u> | — | <u>16</u> | 4 |
| 1g | n-pentyl | <u>15</u> | 11 | — | 8 |
| 1i | H | <u>8</u> | <u>9</u> | 16 | — |

[a] The yields of porphyrin were determined by absorption spectroscopy of small aliquots from the reaction mixture. All reactions gave level 0 scrambling (detected by LD-MS analysis) unless noted otherwise. Reaction conditions: 10 mM reactants and 10 equiv of Zn(OAc)$_2$ in EtOH under reflux exposed to air for 3 h, then treated with 3/4 equiv of DDQ per pyrrole unit (30 mM). The combination that gives the better yield of porphyrin is underlined.
[b] Isolated yield.
[c] Level 2 scrambling.

The results illustrate the effects of substituents (alkyl or aryl) on the yields of the trans-AB-porphyrins and the relative reactivity of those groups when present on the dipyrromethane (1) versus 1,9-bis(dimethylaminomethyl)-dipyrromethane (3). The yields of porphyrin are insensitive to the presence of an alkyl versus aryl group on either dipyrromethane or 1,9-bis(dimethylaminomethyl)-dipyrromethane reactants. However, in the synthesis of porphyrins bearing only one meso-substituent (A-porphyrin), the combination of unsubstituted dipyrromethane and 5-substituted 1,9-bis(dimethylaminomethyl)dipyrromethane affords higher yields than the reverse combination.

Synthesis of trans-AB-, trans-A$_2$-, and A-porphyrins. Scope with diverse substituents. We examined the synthesis of a series of trans-AB-, trans-A$_2$-, and A-porphyrins bearing diverse substituents (Table 5). Each porphyrin was purified by short passage over a pad of silica. 5-(p-Tolyl)dipyrromethane (1b) was reacted with a series of 1,9-bis(dimethylaminomethyl)-dipyrromethanes bearing diverse substituents 3j-m, including acetal,[27] allyl,[27] swallowtail,[28] and carboethoxy[30] groups. In each case, no scrambling was observed and the isolated yields of the trans-AB-porphyrins ranged from 5-15%. In the same manner, a trans-AB-porphyrin (Zn5gh) bearing two alkyl groups was prepared in 17% yield. When a 5-TMS-ethynyldipyrromethane (1n) was employed, the yield of porphyrin was low (Zn5an and Zn5jn). Very little change was obtained upon use of the TMS-ethynyl unit in the bis(N,N-dimethylaminomethyl)dipyrromethane species.

TABLE 5

Synthesis of trans-AB-, A$_2$-, and A-Porphyrins Zn5 with diverse substituents[a]

| | Bis(aminomethyl) dipyrromethane | | Dipyrromethane | Porphyrin | Yield (%)[b] |
|---|---|---|---|---|---|
| | | trans-AB-Porphyrin | | | |
| 3j | 5,5-dimethyl-1,3-dioxan-2-yl | | 1b (p-tolyl) | Zn5bj | 10 |
| 3k | allyl | | 1b (p-tolyl) | Zn5bk | 14 |
| 3l | swallowtail (nonan-5-yl) | | 1b (p-tolyl) | Zn5bl | 15 |
| 3m | carboethoxy (CO$_2$Et) | | 1b (p-tolyl) | Zn5bm | 5 |

TABLE 5-continued

Synthesis of trans-AB-, A$_2$-, and A-Porphyrins Zn5 with diverse substituents[a]

| Bis(aminomethyl) dipyrromethane | | Dipyrromethane | | Porphyrin | Yield (%)[b] |
|---|---|---|---|---|---|
| 3g | pentyl | 1h | hexyl | Zn5gh | 17 |
| 3a | phenyl | 1n | ≡—TMS | Zn5an | 6 |
| 3j | dioxane (dimethyl) | 1n | ≡—TMS | Zn5jn | 1 |
| *A-Porphyrin* | | | | | |
| 3j | dioxane (dimethyl) | 1i | —H | Zn5ij | 12 |
| 3k | allyl | 1i | —H | Zn5ik | 17 |
| 3l | swallowtail | 1i | —H | Zn5il | 20 |
| 3m | —CH$_2$C(O)OEt | 1i | —H | Zn5im | 5 |
| *trans-A$_2$-Porphyrin* | | | | | |
| 3l | swallowtail | 1l | swallowtail | Zn5ll | 15 |

[a]All reactions give level 0 scrambling (assessed by LD-MS analysis). Reaction conditions: 10 mM reactants and 10 equiv of Zn(OAc)$_2$ in refluxing EtOH exposed to air for 2 h, then treated with 3/4 equiv of DDQ per pyrrole unit (30 mM).
[b]Isolated yields.

A similar series of reactions was performed with unsubstituted dipyrromethane (1i) and 5-substituted 1,9-bis(N,N-dimethylaminomethyl)dipyrromethanes 3j-m. The corresponding A-porphyrins (Zn5ij, Zn5ik, Zn5il, and Zn5im) were obtained in yields of 5-20%. Trans-AB-porphyrins bearing a single swallowtail substituent (Zn5bl and Zn5il) were obtained smoothly. A trans-A$_2$-porphyrin (Zn5ll) was obtained by using a dipyrromethane and a bis(N,N-dimethylaminomethyl)-dipyrromethane each bearing swallowtail substituents at the 5-position. The success of these approaches is in contrast to the failure encountered upon attempted reaction of a dipyrromethane-1-carbinol bearing a swallowtail substituent at the 1-position.[29]

In general, the substituents that can be introduced with this method are quite diverse and open up a number of applications. The acetal group (Zn5bj, Zn5ij) can be converted to an aldehyde,[27] the allyl group (Zn5bk, Zn5ik) can be used for surface attachment,[28] the swallowtail group (Zn5bl, Zn5il Zn5ll) can suppress aggregation and thereby increase the solubility of the porphyrin,[29] and the ester (Zn5bm, Zn5im) provides a motif for apical coordination in self-assembly processes.

Examples 1-30

Experimental

General. All $^1$H NMR (400 MHz) and $^{13}$C NMR (100 MHz) spectra were obtained in $CDCl_3$ unless noted otherwise. Porphyrins were analyzed by laser desorption mass spectrometry without a matrix (LD-MS).[21] Fast atom bombardment mass spectrometry (FAB-MS) data are reported for the molecule ion or protonated molecule ion. Column chromatography was performed with flash silica. Each new compound (except salt 4a) was >95% pure as determined by $^1$H NMR spectroscopy. For each zinc porphyrin, only the principal absorption maxima are reported.

Noncommercial compounds. The dipyrromethanes 1a,[18] 1b,[18] 1c,[22] 1d,[23] 1e,[24] 1f,[25] 1g,[19] 1h,[1] 1i,[26] 1j,[27] 1k,[28] 1l,[28] 1m,[30] 1n[31] were prepared using a new method that entails reaction of an aldehyde in 100 equivalents of pyrrole containing a Lewis acid (e.g., $InCl_3$).[32]

Spectroscopic yield determinations. Yields of porphyrin-forming reactions were determined by removal of aliquots from the reaction mixture, treatment with DDQ, followed by absorption spectroscopy of the oxidized product. For example, an ethanol solution of 3a (1.00 mL, 20.0 mM stock solution, 20.0 μmol of 3a) and an ethanol solution of 1b (1.00 mL, 20.0 mM stock solution, 20.0 μmol of 1b) were combined and treated with $Zn(OAc)_2$ (36.6 mg, 200 μmol), affording [3a]=[1a]=10 mM. The reaction mixture was refluxed for a designated period. A sample of DDQ (13.6 mg, 60.0 μmol) was added and the mixture was stirred for 10 min at room temperature, then triethylamine (13 μL, 100 μmol) was added. An aliquot (25 μL) of the reaction mixture was removed and diluted with THF (500 μL, 21 times dilution), then 50 μL of this diluted reaction mixture was added to a cuvette containing 3.00 mL of THF (61 times dilution) and the absorption spectrum was recorded (total dilution 1281 times). The yield of the porphyrin was determined by the intensity of the Soret band (412 nm, $\epsilon$=500,000 $M^{-1}$ $cm^{-1}$) measured from the apex to the base of the red edge of the band. In this manner, a Soret band absorption of 1.00 corresponded to a porphyrin yield of 26%.

Examples 1-2

Standard Procedures

Example 1

Aminomethylation of a dipyrromethane, exemplified for 1,9-bis(N,N-dimethylaminomethyl)-5-phenyldipyrromethane (3a). A solution of 1a (667 mg, 3.00 mmol) in $CH_2Cl_2$ (30 mL) at room temperature was treated with N,N-dimethylmethyleneammonium iodide (Eschenmoser's reagent; employed as a fine powder; 1.17 g, 6.30 mmol). After 1 h, $CH_2Cl_2$ (100 mL) and aqueous $NaHCO_3$ (100 mL) were added to the reaction mixture. The organic phase was dried ($Na_2SO_4$) and then concentrated to dryness. Addition of hexanes/$CH_2Cl_2$ afforded a precipitate, which upon filtration was obtained as a pale yellow solid (600 mg, 59%): mp 76-78° C.; $^1$H NMR δ 2.17 (s, 12H), 3.33 (s, 4H), 5.37 (s, 1H), 5.72-5.74 (m, 2H), 5.89-5.91 (m, 2H), 7.19-7.31 (m, 5H), 8.07-8.18 (br, 2H); $^{13}$C NMR δ 44.3, 45.0, 56.7, 106.8, 107.3, 126.7, 128.36, 128.48, 128.9, 132.5, 142.4; Anal. Calcd for $C_{21}H_{28}N_4$: C, 74.96; H, 8.39; N, 16.65. Found: C, 74.76; H, 8.63; N, 16.27.

Example 2

Porphyrin formation from 1,9-bis(N,N-dimethylaminomethyl)dipyrromethanes, exemplified for Zn(II)-5-mesityl-15-phenylporphyrin (Zn5ac) via 3a+1c. A solution of 3a (168 mg, 0.500 mmol) and 5-mesityldipyrromethane (1c, 132 mg, 0.500 mmol) in ethanol (50 mL) at room temperature was treated with $Zn(OAc)_2$ (917 mg, 5.00 mmol). The mixture was heated to reflux. After 2 h, the reaction mixture was allowed to cool to room temperature. A sample of DDQ (340 mg, 1.50 mmol) was added and the mixture was stirred for 15 min. Triethylamine (355 μL, 2.50 mmol) was added and the reaction mixture was concentrated to dryness. Column chromatography [silica, hexane/$CH_2Cl_2$ (1:1)] afforded a purple solid (42.4 mg, 15%): $^1$H NMR δ 1.85 (s, 6H), 2.68 (s, 3H), 7.34 (s, 2H), 7.80-7.82 (m, 3H), 8.25-8.28 (m, 2H), 9.00 (d, J=4.4 Hz, 2H), 9.14 (d, J=4.4 Hz, 2H), 9.41 (d, J=4.4 Hz, 2H), 9.45 (d, J=4.4 Hz, 2H), 10.30 (s, 2H); $^{13}$C NMR δ 21.7, 22.0, 106.1, 118.7, 120.2, 126.9, 127.7, 128.0, 131.6, 131.9, 132.5, 132.7, 134.8, 137.8, 139.0, 139.6, 142.9, 149.65, 149.74, 150.17, 150.31; Anal Calcd for $C_{35}H_{26}N_4Zn$: C, 74.01; H, 4.61; N, 9.86. Found: C, 74.27; H, 4.72; N, 9.53. LD-MS obsd 565.9, Calcd 566.14 ($C_{35}H_{26}N_4Zn$); $\lambda_{abs}$ 412, 544 nm.

Examples 3-17

Synthesis of 1,9-Dialkylated Dipyrromethanes

Example 3

Hydroiodide salt of 1,9-bis(N,N-dimethylaminomethyl)-5-phenyldipyrromethane (2a). A solution of 1a (222 mg, 1.00 mmol) in $CH_2Cl_2$ (10 Ml) at room temperature was treated with N,N-dimethylmethyleneammonium iodide (fine powder form; 389 mg, 2.10 mmol). After 1 h, the mixture was diluted with ethyl ether (30 Ml), causing formation of a precipitate. A pale yellow solid (542 mg, 91%) was collected by filtration: mp 138-140° C.; $^1$H NMR δ 2.97 (d, J=5.2 Hz, 12H), 4.54 (d, J=5.2 Hz, 4H), 5.45 (s, 1H), 5.79-5.81 (m, 2H), 6.19-6.21 (m, 2H), 7.20-7.29 (m, 5H), 8.90-9.10 (br, 2H), 10.40 (s, 2H); $^{13}$C NMR δ 43.03, 43.08, 44.6, 55.2, 108.9, 113.6, 118.2, 126.7, 128.43, 128.54, 135.0, 143.0; FAB-MS obsd 465.18, calcd 465.16 [(M-I)$^+$] (M=$C_{21}H_{30}IN_4$).

Example 4

Hydroiodide salt of 1,9-bis(N,N-trimethylaminomethyl)-5-phenyldipyrromethane (4a). A solution of 3a (336 mg, 1.00 mmol) in dry $CH_2Cl_2$ (10 Ml) was treated with $CH_3I$ (3.00 mmol) at room temperature in 1 h. The reaction mixture was filtered, washed with a small amount of cold THF, and concentrated to dryness, affording a pale yellow solid (400 mg, 65%, >80% pure): mp 186-188° C.; $^1$H NMR (DMSO-$d_6$) δ 3.37 (s, 18H), 4.80 (s, 4H), 5.90 (s, 1H), 6.18 (s, 2H), 6.69 (s, 2H), 7.60-7.76 (m, 5H), 11.50-11.68 (br, 2H); $^{13}$C NMR (DMSO-d$_6$) δ 43.2, 51.4, 54.37, 54.41, 61.8, 107.9, 113.6, 118.1, 126.7, 128.1, 128.4, 135.8, 1425.4; FAB-MS obsd 493.21; calcd 493.18 [(M-I)$^+$] (M=C$_{23}$H$_{34}$IN$_4$).

Example 5

1,9-Bis(N,N-dimethylaminomethyl)-5-(p-tolyl)dipyrromethane (3b). Following the standard procedure, reaction of 1.00 mmol of 1b afforded a pale yellow solid (320 mg, 91%): mp 62-64° C.; $^1$H NMR δ 2.17 (s, 12H), 2.32 (s, 3H), 3.29-3.38 (m, 4H), 5.34 (s, 1H), 5.74-5.75 (m, 2H), 5.90-5.91 (m, 2H), 7.09 (s, 4H), 8.27-8.35 (br, 2H); $^{13}$C NMR δ 21.3, 44.1, 45.2, 56.9, 106.8, 107.6, 128.4, 128.9, 129.4, 133.1, 136.5, 139.6; FAB-MS obsd 350.2483, calcd 350.2470 (C$_{22}$H$_{30}$N$_4$).

Example 6

1,9-Bis(N,N-dimethylaminomethyl)-5-mesityldipyrromethane (3c). Following the standard procedure, reaction of 1.00 mmol of 1c afforded a pale yellow solid (240 mg, 64%): mp 43-45° C.; $^1$H NMR δ 2.09 (s, 6H), 2.18 (s, 12H), 2.27 (s, 3H), 3.34 (s, 4H), 5.77-5.79 (m, 2H), 5.82 (s, 1H), 5.92-5.93 (m, 2H), 6.83 (s, 2H), 8.18-8.34 (br, 2H); $^{13}$C NMR δ 20.91, 21.03, 38.9, 45.1, 56.8, 106.4, 108.0, 127.9, 130.4, 131.7, 135.1, 136.4, 137.7; FAB-MS obsd 378.2785, calcd 378.2783 (C$_{24}$H$_{34}$N$_4$).

Example 7

1,9-Bis(N,N-dimethylaminomethyl)-5-(4-methoxyphenyl)dipyrromethane (3d). Following the standard procedure, reaction of 1.00 mmol of 1d afforded a pale yellow solid (310 mg, 85%): mp 65-66° C.; $^1$H NMR δ 2.15 (s, 12H), 3.28-3.36 (m, 4H), 3.77 (s, 3H), 5.30 (s, 1H), 5.71-5.73 (m, 2H), 5.90-5.91 (m, 2H), 6.80-6.82 (m, 2H), 7.09-7.11 (m, 2H), 8.30-8.45 (br, 2H); $^{13}$C NMR δ 43.6, 45.2, 55.5, 56.9, 106.9, 107.6, 114.0, 128.9, 129.6, 133.3, 134.8, 158.5; FAB-MS obsd 366.2411, calcd 366.2420 (C$_{22}$H$_{30}$N$_4$O).

Example 8

1,9-Bis(N,N-dimethylaminomethyl)-5-(pentafluorophenyl)dipyrromethane (3e). Following the standard procedure, reaction of 1.00 mmol of 1e afforded a yellow solid (370 mg, 87%): mp 38-40° C.; $^1$H NMR δ 2.19 (s, 12H), 3.30-3.41 (m, 4H), 5.82 (s, 1H), 5.87-5.88 (m, 2H), 5.94-5.95 (m, 2H), 8.50-8.60 (br, 2H); $^{13}$C NMR δ 33.5, 45.2, 56.8, 107.3, 107.9, 116.2-116.5 (m), 128.3, 129.8, 136.5-136.8 (m), 139.0-139.3 (m, two peaks were overlapped), 141.5-141.8 (m), 143.8-144.0 (m), 146.3-146.4 (m); FAB-MS obsd 426.1825, calcd 426.1843 (C$_{21}$H$_{23}$F$_5$N$_4$).

Example 9

1,9-Bis(N,N-dimethylaminomethyl)-5-methyldipyrromethane (3f). Following the standard procedure, reaction of 1.00 mmol of if afforded a pale yellow solid (140 mg, 51%): mp 113-115° C.; $^1$H NMR δ 1.57 (d, J=8.0 Hz, 3H), 2.16 (s, 12H), 3.32 (s, 4H), 4.07-4.12 (m, 1H), 5.87-5.91 (m, 4H), 8.12-8.24 (br, 2H); $^{13}$C NMR δ 20.6, 32.1, 45.1, 56.8, 104.2, 107.4, 128.4, 135.2; FAB-MS obsd 274.31, calcd 274.22 (C$_{16}$H$_{26}$N4).

Example 10

1,9-Bis(N,N-dimethylaminomethyl)-5-n-pentyldipyrromethane (3g). Following the standard procedure, reaction of 1.00 mmol of 1g afforded a brown oil (290 mg, 87%): NMR δ 0.85 (t, J=6.4 Hz, 3H), 1.27 (s, 6H), 1.92-1.94 (m, 2H), 2.37 (s, 12H), 3.59-3.67 (m, 4H), 3.92-3.95 (m, 1H), 5.89-5.90 (m, 2H), 5.97-5.98 (m, 2H), 9.10-9.24 (br, 2H); $^{13}$C NMR δ 14.3, 22.8, 27.5, 31.9, 34.8, 38.2, 45.2, 56.9, 105.0, 107.4, 128.5, 134.1; FAB-MS obsd 330.2774, calcd 330.2783 (C$_{20}$H$_{34}$N$_4$).

Example 11

1,9-Bis(N,N-dimethylaminomethyl)-5-n-hexyldipyrromethane (3h). Following the standard procedure, reaction of 1.00 mmol of 1h afforded a yellow solid (278 mg, 80%): mp 88-90° C.; $^1$H NMR δ 0.85 (t, J=6.4 Hz, 3H), 1.24-1.29 (m, 8H), 1.89-1.91 (m, 2H), 2.16 (s, 12H), 3.29-3.37 (m, 4H), 3.88 (t, J=7.6 Hz, 1H), 5.87-5.90 (m, 4H), 8.10-8.20 (br, 2H); $^{13}$C NMR δ 14.3, 22.8, 27.8, 29.4, 31.9, 34.7, 38.1, 45.2, 56.9, 105.0, 107.4, 128.4, 134.1; FAB-MS obsd 344.2859, calcd 344.2940 (C$_{21}$H$_{36}$N$_4$).

Example 12

1,9-Bis(N,N-dimethylaminomethyl)dipyrromethane (3i). Following the standard procedure with slight modification (K$_2$CO$_3$ was used instead of NaHCO$_3$), reaction of 1.00 mmol of 1i afforded a pale yellow solid (152 mg, 63%): mp 74-76° C.; $^1$H NMR δ 2.17 (s, 12H), 3.33 (s, 4H), 3.84 (s, 2H), 5.82-5.83 (m, 2H), 5.88-5.90 (m, 2H), 8.55-8.70 (br, 2H); $^{13}$C NMR δ 27.0, 45.2, 56.9, 105.9, 107.8, 128.6, 129.7; FAB-MS obsd 261.2091, calcd 261.2079 (C$_{15}$H$_{24}$N$_4$).

Example 13

1,9-Bis(N,N-dimethylaminomethyl)-5-(5,5-dimethyl-1,3-dioxan-2-yl)dipyrromethane (3j). A solution of Fb8a (353 mg, 0.500 mmol) in THF (60 m Following the standard procedure, reaction of 1.00 mmol of 1j afforded a colorless solid (280 mg, 75%): mp 92-94° C.; $^1$H NMR δ 0.72 (s, 3H), 1.12 (s, 3H), 2.18 (s, 12H), 3.32 (d, J=13.2 Hz, 2H), 3.41 (d, J=13.2 Hz, 2H), 3.48 (d, J=13.2 Hz, 2H), 3.72 (d, J=13.2 Hz, 2H), 4.30 (d, J=4.0 Hz, 1H), 4.80 (d, J=4.0 Hz, 1H); 5.79-5.81 (m, 2H), 5.88-5.89 (m, 2H), 8.80-8.90 (br, 2H); $^{13}$C NMR δ 22.0, 23.2, 30.5, 42.6, 45.2, 57.0, 103.7, 107.0, 107.2, 128.8, 129.5; FAB-MS obsd 374.2680, calcd 374.2682 (C$_{21}$H$_{34}$N$_4$O$_2$).

Example 14

5-Allyl-1,9-bis(N,N-dimethylaminomethyl)dipyrromethane (3k). Following the standard procedure, reaction of 1.00 mmol of 1k afforded a brown oil (130 mg, 43%): $^1$H NMR δ 2.14 (s, 12H), 2.68-2.72 (m, 2H), 3.32-3.33 (m, 4H), 4.00-4.03 (m, 1H), 4.98-5.08 (m, 2H), 5.76-5.83 (m, 1H), 5.89-5.90 (m, 4H), 8.20-8.40 (br, 2H); $^{13}$C NMR δ 38.2, 39.3, 45.2, 56.9, 105.2, 107.5, 116.7, 128.6, 133.4, 136.8; FAB-MS obsd 300.2308, calcd 300.2314 (C$_{18}$H$_{28}$N$_4$).

Example 15

1,9-Bis(N,N-dimethylaminomethyl)-5-(tridec-7-yl)dipyrromethane (3l). Following the standard procedure, reaction of 1.00 mmol of 1l afforded a brown oil (180 mg, 81%): $^1$H NMR δ 0.86 (t, J=7.2 Hz, 6H), 1.13-1.35 (m, 20H), 1.81-1.91 (m, 1H), 2.16 (s, 12H), 3.30 (d, J=13.2 Hz, 2H), 3.39 (d, J=13.2 Hz, 2H), 3.97 (d, J=6.4 Hz, 2H), 5.85-5.86 (m, 2H), 5.89-5.90 (m, 2H), 8.15-8.33 (br, 2H); $^{13}$C NMR δ 14.3, 22.9, 27.2, 29.9, 31.6, 32.1, 41.8, 42.1, 45.1, 56.9, 105.9, 107.5, 127.9, 132.9; FAB-MS obsd 442.4033, calcd 442.4035 ($C_{28}H_{50}N_4$).

Example 16

1,9-Bis(N,N-dimethylaminomethyl)-5-(ethoxycarbonyl) dipyrromethane (3m). Following the standard procedure, reaction of 1.00 mmol of 1m afforded a brown oil (230 mg, 69%): $^1$H NMR δ 1.27 (t, J=7.2 Hz, 3H), 2.17 (s, 12H), 3.28 (d, J=12.0 Hz, 2H), 3.45 (d, J=12.0 Hz, 2H), 4.20 (q, J=7.2 Hz, 2H), 4.99 (s, 1H), 5.89-5.93 (m, 4H), 8.80-9.00 (br, 2H); $^{13}$C NMR δ 14.3, 44.6, 45.1, 56.7, 61.8, 106.9, 107.8, 127.2, 129.4, 171.6; FAB-MS obsd 333.2291, calcd 332.2212 ($C_{18}H_{28}N_4O_2$).

Example 17

1,9-Bis(N,N-dimethylaminomethyl)-5-[2-(trimethylsilyl) ethynyl]dipyrromethane (3n) Following the standard procedure, reaction of 1.00 mmol of 1n afforded a brown solid (290 mg, 81%): mp 73-76° C.; $^1$H NMR δ 0.19 (s, 9H), 2.18 (s, 12H), 3.35 (d, J=3.2 Hz, 4H), 5.15 (s, 1H), 5.90-5.91 (m, 2H), 5.96-5.97 (m, 2H), 8.30-8.40 (br, 2H); $^{13}$C NMR δ 0.2, 31.6, 45.2, 56.8, 87.7, 104.1, 106.0, 107.6, 129.1, 129.4.

Examples 18-30

Synthesis of Zn(II) porphyrins

Example 18

Zn(II)-5-(4-Methylphenyl)-15-phenylporphyrin (Zn5ab) via 3a+1b. Following the standard procedure, reaction of 0.500 mmol of 3a and 1b afforded a purple solid (43 mg, 16%): $^1$H NMR δ 2.75 (s, 2H), 7.58-7.62 (m, 2H), 7.77-7.83 (m, 2H), 8.13-8.18 (m, 2H), 8.26-8.29 (m, 2H), 9.11-9.15 (m, 2H), 9.15-9.19 (m, 2H), 9.41-9.47 (m, 2H), 10.31 (s, 2H); $^{13}$C NMR δ 21.7, 106.6, 120.3, 120.6, 127.4, 128.1, 128.2, 132.2, 132.3, 132.7, 132.9, 135.7, 135.8, 137.8, 141.6, 144.6, 150.61, 150.64, 151.0, 151.2; LD-MS obsd 538.5; FAB-MS obsd 538.1150, calcd 538.1136 ($C_{33}H_{22}N_4Zn$); $λ_{abs}$ 413, 539 nm.

Example 19

Zn(II)-5-(5,5-Dimethyl-1,3-dioxan-2-yl)-15-(4-methylphenyl)porphyrin (Zn5bj) via 3j+1b. Following the standard procedure, reaction of 1.00 mmol of 3j and 1b afforded a purple solid (58.0 mg, 10%): $^1$H NMR δ 1.17 (s, 3H), 2.00 (s, 3H), 2.74 (s, 3H), 4.30-4.39 (m, 4H), 7.60 (d, J=8.0 Hz, 2H), 8.07 (s, 1H), 8.14 (d, J=8.0 Hz, 2H), 9.18 (d, J=4.0 Hz, 2H), 9.43 (d, J=4.0 Hz, 2H), 9.56 (d, J=4.0 Hz, 2H), 10.18 (d, J=4.0 Hz, 2H), 10.34 (s, 2H); $^{13}$C NMR (THF-$d_8$) δ 21.7, 23.0, 31.7, 80.8, 106.4, 108.0, 113.2, 121.5, 128.1, 131.8, 132.0, 132.5, 132.9, 135.6, 137.8, 141.6, 150.36, 150.48, 150.51, 151.3; LD-MS obsd 575.9; FAB-MS obsd 576.1519, calcd 576.1504 ($C_{33}H_{28}N_4O_2Zn$); $λ_{abs}$ 409, 541 nm.

Example 20

Zn(II)-5-Allyl-15-(4-methylphenyl)porphyrin (Zn5bk) via 3k+1b. Following the standard procedure, reaction of 1.00 mmol of 3k and 1b afforded a purple solid (70.0 mg, 14%): $^1$H NMR δ 2.75 (s, 3H), 5.15-5.20 (m, 2H), 5.73-5.75 (m, 2H), 6.81-6.88 (m, 1H), 7.61 (d, J=8.0 Hz, 2H), 8.15 (d, J=8.0 Hz, 2H), 9.13 (d, J=4.0 Hz, 2H), 9.36-9.37 (m, 2H), 9.59 (d, J=4.0 Hz, 2H), 10.13 (s, 2H); $^{13}$C NMR (THF-$d_8$) δ 21.8, 40.0, 106.12, 106.18, 115.5, 116.6, 120.1, 128.1, 130.4, 132.2, 132.72, 132.81, 135.7, 137.7, 141.7, 143.7, 150.26, 150.44, 151.26, 151.42; LD-MS obsd 501.9; FAB-MS obsd 502.1118, calcd 502.1136 ($C_{30}H_{22}N_4Zn$); $λ_{abs}$ 412, 545 nm.

Example 21

Zn(II)-5-(4-Methylphenyl)-15-(tridec-7-yl)porphyrin (Zn5bl) via 3l+1b. Following the standard procedure, reaction of 1.00 mmol of 3l and 1b afforded a purple solid (100 mg, 15%): $^1$H NMR δ 0.69-0.72 (m, 6H), 1.06-1.11 (m, 12H), 1.33-1.42 (m, 2H), 1.58-1.66 (m, 2H), 2.75 (s, 3H), 2.80-2.89 (m, 2H), 3.00-3.10 (m, 2H), 5.38-5.42 (m, 1H), 7.60 (d, J=7.6 Hz, 2H), 8.13 (d, J=7.6 Hz, 2H), 9.12-9.14 (m, 2H), 9.39-9.40 (m, 2H), 9.50-9.53 (m, 2H), 9.90 (d, J=4.8 Hz, 1H), 9.99 (d, J=4.8 Hz, 1H), 10.26 (s, 2H); $^{13}$C NMR δ 14.2, 21.8, 22.7, 29.9, 31.9, 43.0, 47.4, 105.7, 106.0, 119.7, 125.0, 127.6, 130.3, 131.3, 131.69, 131.72, 132.1, 132.5, 132.74, 134.77, 137.3, 139.9, 147.7, 149.1, 149.4, 149.72, 149.74, 150.53, 150.58, 152.0; LD-MS obsd 644.7; FAB-MS obsd 644.2899, calcd 644.2857 ($C_{40}H_{44}N_4Zn$); $λ_{abs}$ 412, 545 nm.

Example 22

Zn(II)-5-Ethoxycarbonyl-15-(4-methylphenyl)porphyrin (Zn5bm) via 3m+1b. Following the standard procedure, reaction of 1.00 mmol of 3m and 1b afforded a purple solid (25.0 mg, 5%): $^1$H NMR (THF-$d_8$) δ 1.82 (t, J=7.2 Hz, 3H), 2.73 (s, 3H), 5.08 (q, J=7.2 Hz, 2H), 7.61 (d, J=8.0 Hz, 2H), 8.11 (d, J=7.6 Hz, 2H), 9.04 (d, J=4.4 Hz, 2H), 9.38 (d, J=4.4 Hz, 2H), 9.49 (d, J=4.4 Hz, 2H), 9.66 (d, J=4.8 Hz, 2H), 10.30 (s, 2H); $^{13}$C NMR (THF-$d_8$) δ 14.4, 20.8, 62.2, 106.71, 106.83, 107.3, 127.2, 131.11, 131.15, 132.40, 132.53, 134.7, 137.1, 140.4, 149.2, 149.70, 149.77, 150.1, 172.2; LD-MS obsd 535.6; FAB-MS obsd 534.1059, calcd 534.1034 ($C_{30}H_{22}N_4O_2Zn$); $λ_{abs}$ 410, 541 nm

Example 23

Zn(II)-5-Hexyl-15-n-pentylporphyrin (Zn5gh) from 3g+1h. Following the standard procedure, reaction of 0.600 mmol of 3g and 1h afforded a purple solid (80.0 mg, 17%): $^1$H NMR δ 0.94-1.03 (m, 6H), 1.40-1.46 (m, 2H), 1.51-1.61 (m, 4H), 1.83-1.88 (m, 4H), 2.54-2.59 (m, 4H), 4.94-4.98 (m, 4H), 9.34 (d, J=4.4 Hz, 4H), 9.58 (d, J=4.4 Hz, 4H), 10.00 (s, 2H); $^{13}$C NMR (THF-$d_8$) δ 13.7, 13.8, 22.9, 23.0, 30.4, 32.3, 32.9, 35.28, 35.34, 39.1, 39.4, 104.5, 118.81, 118.82, 128.8, 131.6, 148.9, 150.3; LD-MS obsd 526.6; FAB-MS obsd 526.2088, calcd 526.2075 ($C_{31}H_{34}N_4Zn$); $λ_{abs}$ 411, 546 nm.

Example 24

Zn(II)-5-Phenyl-15-[2-(trimethylsilyl)ethynyl]porphyrin (Zn5an) from 3a+1n. Following the standard procedure, reaction of 1.00 mmol of 3a and 1n afforded a purple solid (30.1 mg, 6%): $^1$H NMR (THF-$d_8$) δ 0.69 (s, 9H), 7.79-7.81 (m, 3H), 8.22-8.24 (m, 2H), 8.79 (d, J=4.4 Hz, 2H), 9.34 (d, J=4.4 Hz, 2H), 9.45 (d, J=4.4 Hz, 2H), 9.85 (d, J=4.4 Hz, 2H), 10.22 (s, 2H); $^{13}$C NMR (THF-$d_8$) δ 0.8, 98.5, 100.2, 106.0, 107.7, 122.5, 127.5, 128.4, 131.9, 132.3, 133.13, 133.24, 135.6, 135.8, 144.3, 150.5, 150.8, 151.0, 153.6; LD-MS obsd 545.5; FAB-MS obsd 544.1061, calcd 544.1062 ($C_{31}H_{24}N_4SiZn$); $λ_{abs}$ 424, 556, 595 nm.

Example 25

Zn(II)-5-(5,5-Dimethyl-1,3-dioxan-2-yl)-15-[2-(trimethylsilyl)ethynyl]porphyrin (Zn5jn) from 3j+1n. Following the standard procedure, reaction of 1.00 mmol of 3j and 1n afforded a purple solid (5.70 mg, 1%): $^1$H NMR δ 7.98 (s, 2H), 9.30 (d, J=4.8 Hz, 2H), 9.40 (d, J=4.8 Hz, 2H), 9.75 (d, J=4.0 Hz, 2H), 10.08 (d, J=4.0 Hz, 2H), 10.11 (s, 2H); LD-MS obsd 583.406; FAB-MS obsd 582.1473, calcd 582.1429 (C$_{31}$H$_{30}$N$_4$O$_2$SiZn); λ$_{abs}$ 417, 551, 587 nm.

Example 26

Zn(II)-5-(5,5-Dimethyl-1,3-dioxan-2-yl)porphyrin (Zn5ij) from 3j+1i Following the standard procedure, reaction of 1.00 mmol of 3j and 1i afforded a purple solid (56.0 mg, 12%): $^1$H NMR δ 1.17 (s, 3H), 2.01 (s, 3H), 4.30-4.40 (m, 4H), 8.09 (s, 1H), 9.41 (s, 4H), 9.53 (d, J=4.0 Hz, 2H), 10.15 (s, 1H), 10.19 (d, J=4.0 Hz, 2H), 10.25 (s, 2H); $^{13}$C NMR (THF-d$_8$) δ 21.6, 30.3, 79.4, 104.4, 104.6, 106.6, 108.8, 112.1, 129.6, 130.5, 130.9, 131.1, 131.4, 132.3, 133.7, 148.52, 148.59, 148.87, 148.90, 149.1, 149.5, 150.3, 152.6; LD-MS obsd 485.6; FAB-MS obsd 486.1057, calcd 486.1034 (C$_{26}$H$_{22}$N$_4$O$_2$Zn); λ$_{abs}$ 403, 535 nm.

Example 27

Zn(II)-5-Allylporphyrin (Zn5ik) from 3k+1i. Following the standard procedure, reaction of 1.00 mmol of 3k and 1i afforded a purple solid (71.2 mg, 17%): $^1$H NMR δ 5.17-5.22 (m, 2H), 5.94-5.96 (m, 2H), 6.89-6.96 (m, 1H), 9.46-9.47 (m, 6H), 9.72-9.73 (m, 2H), 10.17 (s, 1H), 10.19 (s, 2H); $^{13}$C NMR (THF-d$_8$) δ 41.0, 105.51, 105.54, 106.42, 106.46, 116.4, 117.9, 131.2, 133.56, 133.63, 133.65, 144.6, 151.1, 151.4, 151.91, 152.03; LD-MS obsd 412.1; FAB-MS obsd 412.0632, calcd 412.0666 (C$_{23}$H$_{16}$N$_4$Zn); λ$_{abs}$ 406, 538 nm.

Example 28

Zn(II)-5-(Tridec-7-yl)porphyrin (Zn5il) from 3l+1i. Following the standard procedure, reaction of 1.00 mmol of 3l and 1i afforded a purple solid (123 mg, 22%): $^1$H NMR δ 0.67-0.70 (m, 6H), 1.02-1.17 (m, 12H), 1.33-1.43 (m, 2H), 1.60-1.64 (m, 2H), 2.81-2.89 (m, 2H), 3.01-3.07 (m, 2H), 5.40-5.44 (m, 1H), 9.42-9.46 (m, 4H), 9.51 (d, J=4.0 Hz, 1H), 9.54 (d, J=4.0 Hz, 1H), 9.92 (d, J=5.2 Hz, 1H), 10.01 (d, J=5.2 Hz, 1H), 10.13 (s, 1H), 10.25 (s, 2H); $^{13}$C NMR δ 14.2, 22.8, 29.9, 31.9, 43.1, 47.5, 103.8, 105.0, 105.2, 125.5, 130.2, 131.2, 131.63, 131.77, 131.83, 131.98, 132.01, 147.4, 148.7, 148.9, 149.2, 149.55, 149.60, 151.5; LD-MS obsd 555.8; FAB-MS obsd 554.2439, calcd 554.2388 (C$_{33}$H$_{38}$N$_4$Zn); λ$_{abs}$ 406, 538 nm.

Example 29

Zn(II)-5-Ethoxycarbonylporphyrin (Zn5im) from 3m+1i. Following the standard procedure, reaction of 1.00 mmol of 3m and 1i afforded a purple solid (22.0 mg, 5%): $^1$H NMR (THF-d$_8$) δ 1.82 (t, J=7.2 Hz, 3H), 5.09 (q, J=7.2 Hz, 2H), 9.51-9.55 (m, 6H), 9.68 (d, J=4.4 Hz, 2H), 10.35 (s, 2H), 10.37 (s, 1H); $^{13}$C NMR (THF-d$_8$) δ 14.4, 62.2, 105.7, 106.4, 108.8, 131.1, 131.7, 132.33, 132.46, 148.7, 149.50, 149.75, 150.12, 171.8; LD-MS obsd 443.9; FAB-MS obsd 444.0566, calcd 444.0565 (C$_{23}$H$_{16}$N$_4$O$_2$Zn); λ$_{abs}$ 403, 535 nm.

Example 30

Zn(II)-5,15-Bis(tridec-7-yl)porphyrin (Zn5ll) from 3l+1l. Following the standard procedure, reaction of 0.800 mmol of 3l and 1l afforded a purple solid (81.0 mg, 14%): $^1$H NMR δ 0.68-0.71 (m, 12H), 1.01-1.14 (m, 24H), 1.31-1.39 (m, 4H), 1.54-1.62 (m, 4H), 2.76-2.85 (m, 4H), 2.97-3.07 (m, 4H), 5.32-5.37 (m, 2H), 9.46-9.50 (m, 4H), 9.84-9.86 (m, 2H), 9.92-9.94 (m, 2H), 10.21 (s, 2H); $^{13}$C NMR δ 14.2, 22.7, 29.8, 31.9, 42.8, 47.2, 104.93, 105.21, 105.49, 124.0, 130.02, 130.25, 130.95, 131.17, 131.50, 131.82, 147.12, 147.37, 149.18, 149.45, 149.72, 149.76, 152.04, 152.10; LD-MS obsd 736.0; FAB-MS obsd 736.4412, calcd 736.4422 (C$_{46}$H$_{64}$N$_4$Zn); λ$_{abs}$ 412, 548 nm.

REFERENCES

1. Rao, P. D.; Dhanalekshmi, S.; Littler, B. J.; Lindsey, J. S. *J. Org. Chem.* 2000, 65, 7323-7344.
2. Brückner, C.; Posakony, J. J.; Johnson, C. K.; Boyle, R. W.; James, B. R.; Dolphin, D. *J. Porphyrins Phthalocyanines* 1998, 2, 455-465.
3. Geier, G. R., III; Callinan, J. B.; Rao, P. D.; Lindsey, J. S. *J. Porphyrins Phthalocyanines* 2001, 5, 810-823.
4. (a) Markovac, A.; MacDonald, S. F. *Can. J. Chem.* 1965, 43, 3364-3371. (b) Clarke, O. J.; Boyle, R. W. *Tetrahedron Lett.* 1998, 39, 7167-7168.
5. Arsenault, G. P.; Bullock, E.; MacDonald, S. F. *J. Am. Chem. Soc.* 1960, 82, 4384-4389.
6. Baldwin, J. E; Crossley, M. J.; Klose, T.; O'Rear, E. A. III; Peters, M. K. *Tetrahedron* 1982, 38, 27-39.
7. Brückner, C.; Posakony, J. J.; Johnson, C. K.; Boyle, R. W.; James, B. R.; Dolphin, D. *J. Porphyrins Phthalocyanines* 1998, 2, 455-465.
8. Tabushi. I; Sakai, K.-i.; Yamamura, K. *Tetrahedron Lett.* 1978, 19, 1821-1824.
9. (a) Westall, R. G. *Nature* 1952, 170, 614-616. (b) Cookson, G. H.; Rimington, C. *Nature* 1953, 171, 875-876. (c) Shemin, D.; Russell, C. S. *J. Am. Chem. Soc.* 1953, 75, 4873-4874. (d) Cookson, G. H.; Rimington, C. *Biochem. J.* 1954, 57, 476-484.
10. (a) Bachman, G. B.; Heisey, L. V. *J. Am. Chem. Soc.* 1946, 68, 2496-2499. (b) Herz, W.; Dittmer, K; Cristol, S. J. *J. Am. Chem. Soc.* 1947, 69, 1698-1700.
11. Schreiber, J.; Maag, H.; Hashimoto, N.; Eschenmoser, A. *Angew. Chem. Int. Ed.* 1971, 10, 330-331.
12. (a) Eisner, U.; Linstead, R. P. *J. Chem. Soc.* 1955, 3742-3749. (b) Eisner, U.; Linstead, R. P.; Parkes, E. A.; Stephen, E. *J. Chem. Soc.* 1956, 1655-1661. (c) Eisner, U. *J. Chem. Soc.* 1957, 854-858. (d) Eisner, U.; Lichtarowicz, A.; Linstead, R. P. *J. Chem. Soc.* 1957, 733-739. (e) Bullock, E.; Johnson, A. W.; Markham, E.; Shaw, K. B. *J. Chem. Soc.* 1958, 1430-1440. (f) Friedman, M. *J. Org. Chem.* 1965, 30, 859-863. (g) Egorova, G. D.; Solev'ev, K. N.; Shul'ga, A. M. *J. Gen. Chem. USSR* 1967, 37, 333-336. (h) Whitlock, H. W.; Hanauer, R. *J. Org. Chem.* 1968, 33, 2169-2171. (i) Kinoshita, H.; Tanaka, S.; Nishimori, N.; Dejima, H.; Inomata, K. *Bull. Chem. Soc. Jpn.* 1992, 65, 2660-2667. (j) Tabushi, I.; Sakai, K.-i.; Yamamura, K. *Tetrahedron Lett.* 1978, 19, 1821-1824.
13. Nguyen, L. T.; Senge, M. O.; Smith, K. M. *Tetrahedron Lett.* 1994, 35, 7581-7584.
14. Nguyen, L. T.; Senge, M. O.; Smith, K. M. *J. Org. Chem.* 1996, 61, 998-1003.
15. Siri, O.; Smith, K. M. *Tetrahedron Lett.* 2003, 44, 6103-6105.
16. (a) Dolphin, D.; Rettig, S. J.; Tang, H.; Wijesekera, T.; Xie, L. Y. *J. Am. Chem. Soc.* 1993, 115, 9301-9302. (b) Boyle, R. W.; Xie, L. Y.; Dolphin, D. *Tetrahedron Lett.* 1994, 35, 5377-5380. (c) Xie, L. Y.; Boyle, R. W.; Dolphin, D. *J. Am. Chem. Soc.* 1996, 118, 4853-4859.
17. (a) Hombrecher, H. K.; Horter, G. *Liebigs Ann. Chem.* 1991, 219-227. (b) Hombrecher, H. K.; Horter, G.; Arp, C. *Tetrahedron* 1992, 48, 9451-9460. (c) Schell, C.; Hombrecher, H. K. *Bioorg. Med. Chem.* 1999, 7, 1857-1865. (d) Schell, C.; Hombrecher, H. K. *Chem. Eur. J.* 1999, 5, 587-598.
18. Mizutani, T.; Ema, T.; Tomita, T.; Kuroda, Y.; Ogoshi, H. *J. Am. Chem. Soc.* 1994, 116, 4240-4250.
19. Hammel, D.; Erk, P.; Schuler, B.; Heinze, J.; Müllen, K. *Adv. Mater.* 1992, 4, 737-739.

20. Littler, B. J.; Ciringh, Y.; Lindsey, J. S. *J. Org. Chem.* 1999, 64, 2864-2872.
21. Srinivasan, N.; Haney, C. A.; Lindsey, J. S.; Zhang, W.; Chait, B. T. *J. Porphyrins Phthalocyanines* 1999, 3, 283-291.
22. Lee, C.-H.; Lindsey, J. S. *Tetrahedron* 1994, 50, 11427-11440.
23. Lee, C.-H.; Kim, J.-Y. *Bull. Korean Chem. Soc.* 1996, 17, 215-217.
24. Boyle, R. W.; Karunaratne, V.; Jasat, A.; Mar, E. K.; Dolphin, D. *Synlett* 1994, 939-940.
25. Oddo, B.; Cambieri, F. *Gazz. Chim. Ital.* 1940, 70, 559-564.
26. Wang, Q. M.; Bruce, D. W. *Synlett* 1995, 1267-1268.
27. Balakumar, A.; Muthukumaran, K.; Lindsey, J. S. *J. Org. Chem.* 2004, 69, 5112-5115.
28. Liu, Z.; Yasseri, A. A.; Loewe, R. S.; Lysenko, A. B.; Malinovskii, V. L.; Zhao, Q.; Surthi, S.; Li, Q.; Misra, V.; Lindsey, J. S.; Bocian, D. F. *J. Org. Chem.* 2004, 69, 5568-5577.
29. Thamyongkit, P.; Speckbacher, M.; Diers, J. R.; Kee, H. L.; Kirmaier, C.; Holten, D.; Bocian, D. F.; Lindsey, J. S. *J. Org. Chem.* 2004, 69, 3700-3710.
30. Trova, M. P.; Gauuan, P. J. F.; Pechulis, A. D.; Bubb, S. M.; Bocckino, S. B.; Crapo, J. D.; Day, B. J. *Bioorg. Med. Chem.* 2003, 11, 2695-2707.
31. Wilson, G. S.; Anderson, H. L. *Synlett* 1996, 1039-1040.
32. Laha, J. K.; Dhanalekshmi, S.; Taniguchi, M.; Ambroise, A.; Lindsey, J. S. *Org. Process Res. Dev.* 2003, 7, 799-812.

The foregoing is illustrative of the present invention, and is not to be construed as limiting thereof. The invention is defined by the following claims, with equivalents of the claims to be included therein.

That which is claimed is:

1. A compound of Formula I:

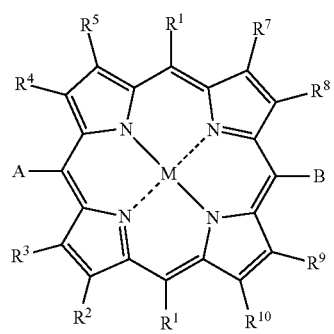

(I)

wherein:

A is a hydrophilic group or a bioconjugatable group;

B is a hydrophilic group when A is a bioconjugatable group, or B is a bioconjugatable group when A is a hydrophilic group;

subject to the proviso that at least one of A and B is non-aromatic;

$R^1$ is selected from the group consisting of H, alkyl and aryl;

$R^2$, $R^3$, $R^4$, $R^5$, $R^7$, $R^8$, $R^9$, and $R^{10}$ are each independently selected from the group consisting of H, halo, loweralkoxy, and loweralkylthio; and M is a metal or a pair of hydrogen atoms.

2. A compound of claim 1, subject to the proviso that both A and B are nonaromatic.

3. A compound of claim 1, wherein each said hydrophilic group is a polyol or polyalkylene oxide group.

4. A compound of claim 3, wherein each said hydrophilic group is selected from the group consisting of pol(propylene glycol), poly(ethylene glycol), and polyethylene-polypropylene glycol.

5. A compound of claim 1, wherein each said bioconjugatable group is selected from the group consisting of amines, acids, aldehydes, sulfonyl chlorides, sulfonyl hydrazides, epoxides, hydroxyl groups, thiol groups, maleimides, aziridines, acryloyls, halo groups, biotin, and 2-iminobiotin.

6. A compound of claim 1, wherein:

each said hydrophilic group is selected from the group consisting of pol(propylene glycol), poly(ethylene glycol), and polyethylene-polypropylene glycol; and each said bioconjugatable group is selected from the group consisting of amines, acids, aldehydes, sulfonyl chlorides, sulfonyl hydrazides, epoxides, hydroxyl groups, thiol groups, maleimides, aziridines, acryloyls, halo groups, biotin, and 2-iminobiotin.

* * * * *

UNITED STATES PATENT AND TRADEMARK OFFICE
CERTIFICATE OF CORRECTION

PATENT NO. : 8,212,023 B2  
APPLICATION NO. : 13/014914  
DATED : July 3, 2012  
INVENTOR(S) : Lindsey et al.

Page 1 of 3

It is certified that error appears in the above-identified patent and that said Letters Patent is hereby corrected as shown below:

In the Specification:
Column 4, Scheme 1: Please correct

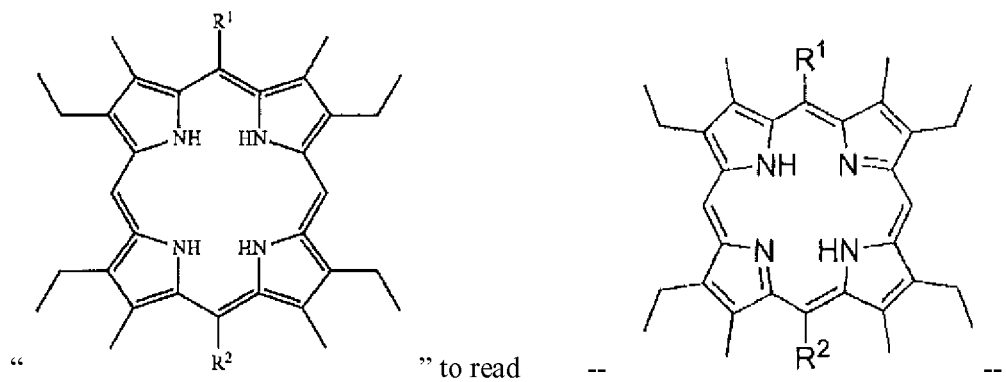

" to read --                    --

Column 21, Table 1, footnote b: Please correct "from the reaction mixture"
to read -- from the reaction mixture. --

Column 26, Line 20: Please correct "condensation of a dipyrromethane 1,9-bis(N,"
to read -- condensation of a dipyrromethane + 1,9-bis(N, --
Line 24: Please correct "-dipyrromethane+a     5-substituted-"
to read -- -dipyrromethane + a 5-substituted- --

Signed and Sealed this
Twenty-fifth Day of February, 2014

Michelle K. Lee
*Deputy Director of the United States Patent and Trademark Office*

Columns 29-30, Table 4: Please correct
TABLE 4-continued
Formation of trans-AB- and A-Porphyrins ZnS via 3a-g,i + 1a-g,i[a]
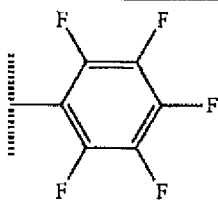
| | | | 4 | 8[c] | 2 |
|---|---|---|---|---|---|
| 1f | methyl | 12 | — | 16 | 4 |
| 1g | n-pentyl | 15 | 11 | — | 8 |
| 1i | H | 8 | 9 | 16 | — |
to read
TABLE 4-continued
Formation of trans-AB- and A-Porphyrins ZnS via 3a-g,i + 1a-g,i[a]
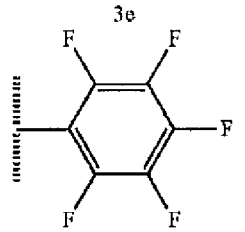
| | | 3f methyl | 3g n-pentyl | 3i H |
|---|---|---|---|---|
| 1e | | — | 4 | 8[c] | 2 |
| 1f | methyl | 12 | | 16 | 4 |
| 1g | n-pentyl | 15 | 11 | — | 8 |
| 1i | H | 8 | 9 | 16 | — |

CERTIFICATE OF CORRECTION (continued)

Column 31, Table 5, items 3g, 3a, 3j: Please add -- *trans*-AB-Porphyrin -- to the first portion of the Table so it will read as follows:

Synthesis of trans-AB-, A$_2$-, and A-Porphyrins Zn5 with diverse substituents[a]

| Bis(aminomethyl) dipyrromethane | | Dipyrromethane | | Porphyrin | Yield (%)[b] |
|---|---|---|---|---|---|
| trans-AB-Porphyrin | | | | | |
| 3g | 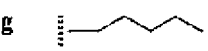 | 1h |  | Zn5gh | 17 |
| 3a | 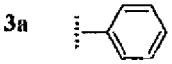 | 1n | —TMS | Zn5an | 6 |
| 3j | 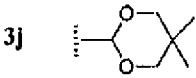 | 1n | 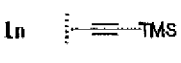—TMS | Zn5jn | 1 |

Column 33, Line 51: Please correct "(412 nm, $\epsilon$=500,000"
        to read -- (412 nm, $\varepsilon$=500,000 --

Column 36, Line 2: Please correct "NMR δ 0.85" to read -- $^1$H NMR δ 0.85 --

Column 38, Line 33: Please correct "541 nm" to read -- 541 nm. --

Column 39, Line 7: Please correct "from 3j+Following"
        to read -- from 3j + 1n. Following --